United States Patent
Alt et al.

(10) Patent No.: US 8,359,097 B2
(45) Date of Patent: Jan. 22, 2013

(54) METHOD OF DETECTING SLEEP APNEA AND TREATMENT THEREOF

(76) Inventors: Eckhard Alt, Houston, TX (US); Maik Gollasch, Berlin (DE)

( * ) Notice: Subject to any disclaimer, the term of this patent is extended or adjusted under 35 U.S.C. 154(b) by 48 days.

(21) Appl. No.: 12/931,152

(22) Filed: Jan. 25, 2011

(65) Prior Publication Data

US 2011/0190642 A1    Aug. 4, 2011

Related U.S. Application Data

(63) Continuation-in-part of application No. 12/807,706, filed on Sep. 10, 2010, which is a continuation-in-part of application No. 12/857,140, filed on Aug. 16, 2010, now Pat. No. 8,219,198, which is a continuation of application No. 11/104,389, filed on Apr. 11, 2005, now Pat. No. 7,778,709, which is a continuation-in-part of application No. 10/622,184, filed on Jul. 16, 2003, which is a continuation-in-part of application No. 10/155,771, filed on May 25, 2002, now Pat. No. 6,829,503.

(30) Foreign Application Priority Data

Oct. 1, 2001    (DE) .................................. 101 48 440

(51) Int. Cl.
*A61N 1/365*    (2006.01)
(52) U.S. Cl. ............................................. 607/20; 607/3
(58) Field of Classification Search ................ 607/3, 17, 607/18, 20, 35
See application file for complete search history.

(56) References Cited

U.S. PATENT DOCUMENTS

| | | | |
|---|---|---|---|
| 4,702,253 A * | 10/1987 | Nappholz et al. ............... | 607/20 |
| 4,919,136 A * | 4/1990 | Alt .................................. | 607/20 |
| 5,003,976 A | 4/1991 | Alt | |
| 5,056,519 A | 10/1991 | Vince | |
| 6,076,015 A * | 6/2000 | Hartley et al. .................. | 607/20 |
| 6,415,183 B1 | 7/2002 | Scheiner et al. | |
| 6,574,507 B1 * | 6/2003 | Bonnet ........................... | 607/20 |
| 6,641,542 B2 | 11/2003 | Cho et al. | |
| 6,752,765 B1 * | 6/2004 | Jensen et al. ................... | 600/536 |
| 7,357,775 B1 | 4/2008 | Koh | |
| 7,371,220 B1 | 5/2008 | Koh et al. | |
| 7,706,881 B1 | 4/2010 | Benser | |
| 2003/0055348 A1 | 3/2003 | Chazal et al. | |
| 2003/0195571 A1 * | 10/2003 | Burnes et al. ..................... | 607/9 |
| 2005/0234313 A1 | 10/2005 | Rowlandson et al. | |

* cited by examiner

*Primary Examiner* — Brian T Gedeon

(57) ABSTRACT

A method is presented for evaluating whether an episode of sleep apnea is occurring in a patient suffering from chronic sleep apnea disorder, for delivery of appropriate therapy. The method, performed by an implantable device, includes sensing the patient's EKG signal and using electrical energy generated by the heart to power subsequent signal processing. This signal is applied as the sole input to a differential signal processing circuit for passage through both a high impedance path and a substantially lower impedance path and amplification of the difference in magnitude between the resulting two signals, to determine changes in the patient's thoracic impedance. Based on such changes, the presence or absence of patient ventilation is detected, to enable an assessment of whether an episode of sleep apnea is occurring. An actual episode of sleep apnea is deemed to have occurred if lack of ventilation exceeds a predetermined interval of time between otherwise regular respiratory cycles. If sleep apnea is indicated, the appropriate therapy is delivered by the device to induce ventilation and halt the apnea episode.

34 Claims, 11 Drawing Sheets

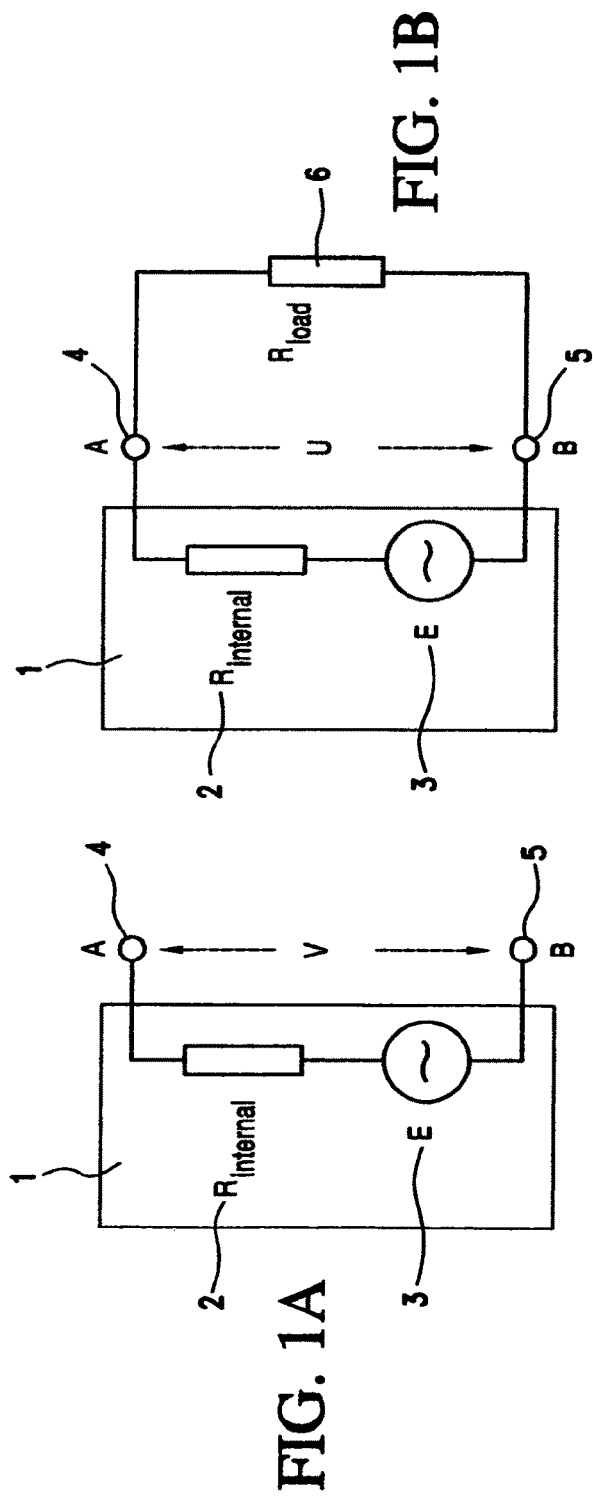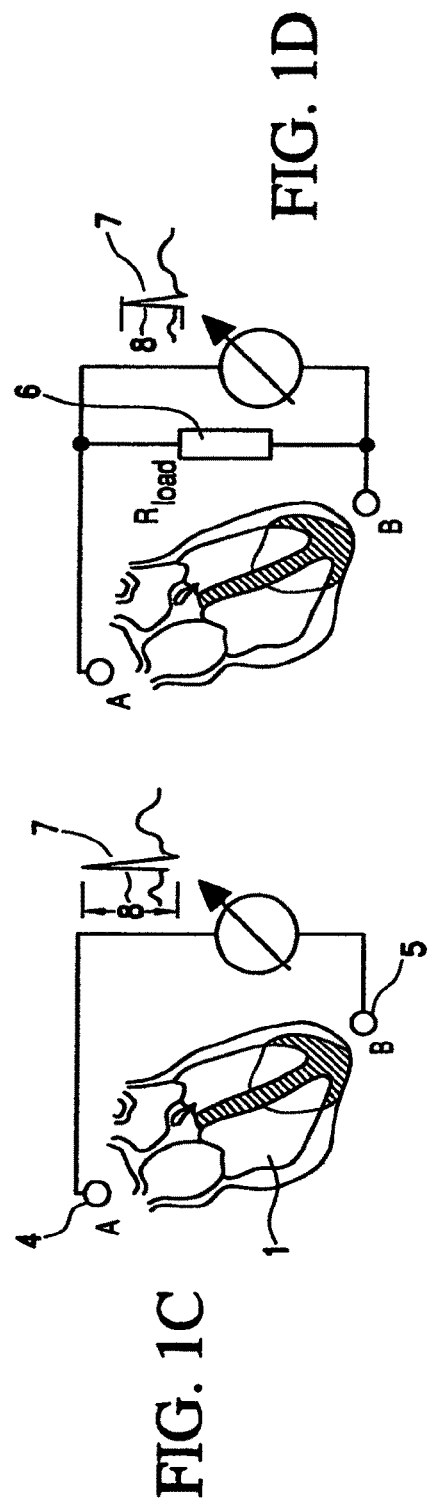

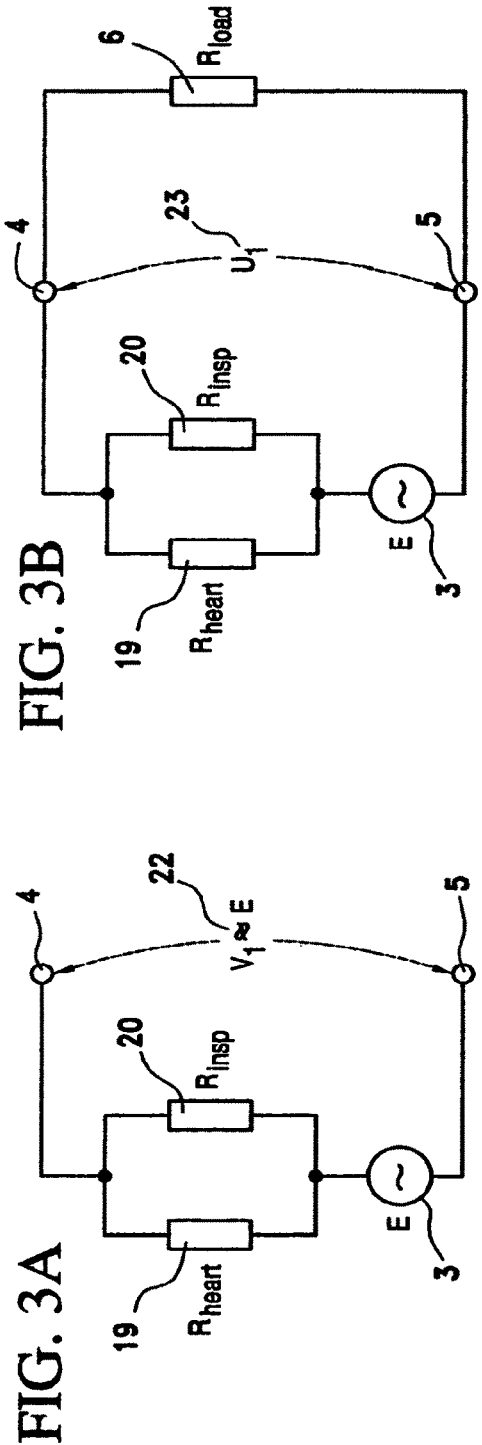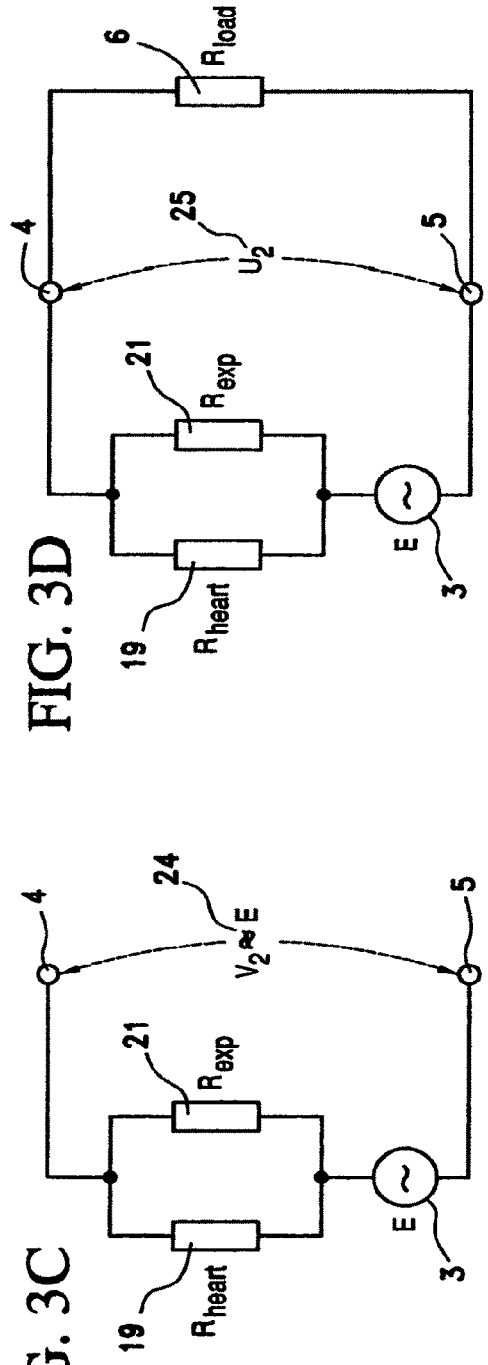
FIG. 3A FIG. 3B FIG. 3C FIG. 3D

METHOD OF DETECTING SLEEP APNEA AND TREATMENT THEREOF

CROSS-REFERENCE TO RELATED APPLICATIONS

This application is a continuation-in-part of Ser. No. 12/807,706 filed Sep. 10, 2010, which is a continuation-in-part of Ser. No. 12/857,140, now U.S. Pat. No. 8,219,198, filed Aug. 16, 2010, which is a continuation of Ser. No. 11/104,389, now U.S. Pat. No. 7,778,709 filed Apr. 11, 2005, which is a continuation-in-part of Ser. No. 10/622,184 filed Jul. 16, 2003, which is a continuation-in-part of Ser. No. 10/155,771, now U.S. Pat. No. 6,829,503, filed May 25, 2002 that claims priority of German patent 10148440-2 filed Oct. 1, 2001 of the same applicant, each of which applications is incorporated by reference in its entirety herein. Applicant claims priority of the aforesaid applications with respect to common subject matter.

BACKGROUND OF THE INVENTION

The present invention relates generally to an improved method of treating a patient diagnosed with sleep apnea. The invention encompasses treating the patient by phrenic nerve stimulation (PNS) from an implanted stimulator device whose output is delivered to stimulate the patient's diaphragm to cause contraction, followed by relaxation, toward establishing a more normal breathing pattern upon detection of an episode of sleep apnea of a certain form or forms. Detection is achieved by sensing the electrical signal (EKG) generated solely by the heart without intervention of external signals applied to the heart, and to apply the sensed signals as the sole input to signal monitoring circuitry from which to determine the thoracic impedance and, therefrom, the ventilatory status of the patient.

Specific resistance of biological materials and impedance measurements have played a major role in modern medicine. The electrical conductivity and capacity of disperse systems have been described as early as 1931 (Fricke et al., *The Electric Conductivity of and Capacity of Dispersed Systems*; Physics 1931; 1:106-115). Later, especially in the 1950s and 1960s, significant interest was directed towards the resistance of biological materials (e.g., Geddes L. et al., *The Specific Resistance of Biological Material: A Compendium of Data for the Biomedical Engineer and Physiologist*, Medical and Biological Engineering 1967, 5:271-293). The application of impedance and resistance measurements for cardio-circulatory function by measuring the blood and body temperature has been studied extensively by Geddes et al., Medical and Biological Engineering 1967, 11:336-339). Also, internal and external whole body impedance measurements have been used for noninvasive monitoring and determination of cardiac output (Carter et al., Chest 2004, 125:1431-1440). In addition, the feasibility of using intracardiac impedance measurements has been evaluated by E. Alt et al. for capture detection in connection with cardiac pacing (Pace 1992, 15:1873-1879).

Background patents that describe the use of impedance in conjunction with implantable devices are referenced in U.S. Pat. No. 5,003,976 to Alt ("the '976 patent"), which describes the cardiac and pulmonary physiological analysis via intracardiac measurements with a single sensor. The '976 patent discloses that a single functional parameter, namely intracardiac impedance, varies both with the intrathoracic pressure fluctuations following respirations and with cardiac contraction. This value is representative of both pulmonary activity and cardiac activity, and can be used as well to monitor the patient's condition and cardio-circulatory status.

It is known that measurement of intracardiac impedance and associated determination of pulmonary activity is useful for detecting episodes of apnea. Many individuals suffer from apnea, which typically occurs during periods of sleep. Hence, the term "sleep apnea" has evolved, although it is possible that apnea in one or more of its forms may occur even while an individual is awake. With apnea, respiration is significantly reduced and may cease entirely for one minute or longer. In the case of sleep apnea, episodes may occur quite frequently, causing the individual to awaken from sleep as these episodes occur. In extreme cases, the individual may die from lack of oxygen (blood oxygen depletion, or hypoxia). At least three forms of sleep apnea are known.

In central sleep apnea or CSA, the condition appears to emanate from neurological causes. As frequency of the episodes of apnea increase, blood oxygen levels decrease and carbon dioxide levels increase. When the $CO_2$ level in the blood becomes excessive, respiratory control nerve centers in the brain respond by generating signals to the phrenic nerves, which in turn, generate nerve signals to the diaphragm and chest wall muscles, causing them to expand the lungs to produce inhalation. But in patients with disturbed respiratory control in the brain, during the periods the $CO_2$ level is increasing, the nerve signals fail to be generated with normal regularity, which means sleep can be disrupted frequently as the cycle of lowering blood oxygen level and increasing $CO_2$ level continues until the nerves respond to awaken the patient. Or, in the worst case, until the ventilatory function fails and the individual expires.

In another form of sleep apnea, the episodes are caused by Cheyne-Stokes Respiration or CSR, an abnormal respiratory pattern characterized by alternating periods of hypopnea and hyperpnea. Hypopnea, like apnea, is a period of significantly reduced or diminished respiration, but unlike apnea, respiration continues albeit reduced, rather than ceasing entirely albeit usually only temporarily. Hyperpnea, on the other hand, is a period of fast, deep breathing. With CSR, the condition is attributable to a lag between the actual blood $CO_2$ level and the time the respiratory control nerve centers of the brain sense that level. As a result, the respiratory control nerve centers generate signals to produce an increase in the depth and frequency of breathing in response to an apparent high blood $CO_2$ level, when in fact the actual level has decreased. Then the brain's respiratory control nerve centers detect the drop in blood $CO_2$ level and act to slow respiration, when in fact the actual level has increased. This causes an increasingly unbalanced cycle of respiration that alternates between hypopnea and hyperpnea, which may become so severe that breathing ceases between the periods of hyperpnea, a condition referred to frank apnea. The episodes of apnea can cause patient arousal from sleep because of blood oxygen depletion, but the arousal typically is brief (only a few seconds) and may occur numerous times during a single night. Here also, a worst case situation is possible. CSR is often (but not necessarily) associated with congestive heart failure (CHF). From time to time herein, this form of sleep apnea may be referred to as CSR, but it will be understood that the meaning of that terminology is CSR-induced apnea or apnea attributable to CSR.

A third form of sleep apnea is obstructive sleep apnea or OSA, which is caused by temporary blockage of the individual's ventilation airway. This condition is attributable to weakness of the muscles around the soft palate, occurring most often in individuals with obesity or with increasing age, such that during sleep these muscles relax and the soft palate assumes a position that obstructs the airway. As a result of this blockage, inadequate amounts of oxygen are delivered to the lungs and the blood $CO_2$ level increases, to a point that the response of the respiration control nerve centers of the brain act typically to awaken the individual for resumption of normal breathing until the next obstruction of the airway occurs.

Various techniques have been advanced in an effort to correct the several forms of sleep apnea. In the case of CSA, detection of an episode by an implanted device may be responded to by direct electrical stimulation of the phrenic nerves from the device via transvenously implanted leads and electrodes whereby to deliver periodic stimulation signals from the phrenic nerves to the diaphragm to cause the latter to cyclically contract and relax in resumption of normal respiratory rhythm. This type of phrenic nerve stimulation therapy or so-called diaphragmatic pacing is described, for example, in U.S. Pat. Nos. 5,056,519 to Vince; 6,415,183 to Scheiner et al.; and 6,641,542 to Cho et al.

If the sleep apnea is attributable to CSR, proposed treatment techniques may address alleviation of the typical source of the disorder, namely CHF, through cardiac pacing alone, as described, for example, in U.S. Pat. No. 7,706,881 to Benser. However, Benser suggests a sustained increase in cardiac output, rather than detection of and response to individual episodes, for suppressing apnea/hypopnea, and states that the increase is beneficial in and of itself by tending to mitigate CHF and pulmonary edema. Alternatively, diaphragmatic pacing attributable to phrenic nerve stimulation may be used as the therapy for suppressing or terminating the apnea induced by CSR, as described for example, in U.S. Pat. No. 7,371,220 to Koh et al ("the '220 patent").

In the case of OSA, a conventional treatment involves nightly wearing by the patient of breathing apparatus that provides continuous positive airway pressure or bi-level positive pressure therapy. It has also been suggested that direct electrical stimulation of muscle adjacent or near the soft palate from an implanted device responsive to episodes of OSA may be suitable to produce sufficient toning of the muscle so as to remove obstruction of the airway and enable resumption of normal breathing pattern, as described, for example, in the '220 patent.

In some instances, a combination of therapies, such as cardiac pacing and diaphragmatic pacing (phrenic nerve stimulation, or PNS) may be used to achieve the desired restoration of normal or near normal breathing pattern, depending on the particular condition or types of condition suffered by the patient, as disclosed, for example, in U.S. Pat. No. 7,357,775 to Koh ("the '775 patent"). In any of these various forms of sleep apnea, it has also been suggested as desirable to generate warning signals as by vibration or tickle voltage from the implanted device or by telemetry to a bedside alarm or monitor to awaken the patient, in addition to delivery of the therapy or if the therapy is proving ineffective, during a detected episode.

In some cases, these forms of therapy are delivered continuously while the patient is asleep, without regard to whether an episode of sleep apnea is occurring. It would be desirable to detect each episode of sleep apnea as it occurs, and thereupon deliver the appropriate therapy rather than to deliver continuous albeit unneeded therapy.

It has been found that cessation of respiration for a period of time may not be truly indicative of onset of an episode of sleep apnea. That is, it may constitute a false detection of apnea, or a false positive, when in fact the patient is otherwise experiencing proper breathing. To avoid false positives, and the consequent delivery of an unnecessary therapy, a conventional technique employed in detection of an episode of sleep apnea is to suppress delivery of therapy unless little or no respiration is detected for a period of time exceeding, for example, twenty seconds as satisfaction that an episode is indeed occurring. However, this technique has the disadvantage that it may prevent prompt detection of actual apnea, with concomitant delay in delivery of appropriate therapy.

Various techniques have been advanced in the art for detecting episodes of sleep apnea (whether or not including hypopnea), as disclosed, for example, in the '220 patent; U.S. patent application Ser. No. 10/795,009 of Koh; and the '775 patent. Once an episode of sleep apnea is detected, therapy is delivered to terminate the episode and restore more normal respiration.

A technique for detecting thoracic impedance and ventilatory status of an individual from information derived by sensing cardiac signals generated by electrical energy of the heart alone is disclosed in the aforementioned related co-pending U.S. patent application Ser. No. 12/807,706 ("the '706 patent application) of the same inventors as in the present application. The sensed cardiac signals are applied as the sole input to signal detection circuitry, from which a factor or parameter related to intrathoracic, intracardiac or thoracic impedance and ventilation function of the patient is derived, and to changes in that impedance and ventilation, as an indication of the status of a physical condition of the patient, in particular, congestive heart failure and treatment thereof.

Prior reported attempts to determine impedance measurements and/or associated ventilatory status of a patient from internal signals in the body had used external (to the heart) power sources to stimulate the heart or to provide currents through the thorax. The resulting cardiac signals or current amplitudes in the thorax were then sensed and applied to detection devices for monitoring and measuring impedance and/or associated ventilatory status. This external energy might be applied either from an implantable device using energy from its own battery or from a supply external to the body.

SUMMARY OF THE INVENTION

It is a principal aim of the present invention to provide an improved method of detecting the thoracic impedance changes of a patient suffering from episodic sleep apnea, and to discern therefrom the pulmonary status and ventilatory activity of the patient, from which to detect onset of an episode of CSA or of CSR-induced apnea and thereupon generate appropriate phrenic nerve stimulation and consequent diaphragmatic pacing, or in the case of detection of onset of an episode of OSA, to provide another type of appropriate stimulation, to terminate the sleep apnea when and as it occurs and to restore normal breathing.

Another important aim of the invention is to provide a method to detect each individual episode of sleep apnea as it occurs, and thereupon to deliver the appropriate therapy from an implanted nerve stimulator, rather than provide possibly harmful continuous therapy even when unneeded.

According to a preferred mode of practicing the invention, a device implantable into the body of the patient of interest is utilized to perform the method, although alternatively, the method could be performed by other means at least partly external to the body. The implantable device may be characterized as an electrical excitation stimulator, and is implemented with circuitry and a battery within a case or can impermeable to body fluids in a conventional manner. The essence of the invention resides in the technique employed for determining thoracic impedance, and therefrom, the patient's ventilatory status, from which to detect onset of each individual episode of sleep disordered or sporadic breathing, i.e., sleep apnea. The electrical signal (EKG) emanating from the heart itself (i.e., without any artificial excitation from sources external to the heart) is sensed by the device as the heart undergoes its cardiac cycle.

A lead or leads and associated electrodes or other sensors electrically coupled to the device are employed to sense the EKG signal at a site relatively remote from the heart itself, and in particular in a preferred embodiment or mode of the invention, in the vicinity of the patient's phrenic nerve.

According to another aspect of the invention, the sensing electrode(s) may be used at least in part to apply electrical stimuli to the phrenic nerve(s) when needed for delivery of appropriate therapy. Importantly, in the present invention the sensed EKG signal is applied as the sole input to differential signal processing circuitry for ascertaining changes in the thoracic impedance of the patient. Based on these changes, the respiratory status of the patient may be determined, and specifically the presence or absence of ventilation. Absence of ventilation is indicative of possible onset of an episode of sleep apnea. And, if desired, the device may be programmed to commence delivery of therapy, by way of electrical stimulation of the phrenic nerve, only after a relatively brief but sustained period of absence of ventilation rather than immediately upon its determination.

The differential signal processing circuit of the device passes the sensed EKG signal through both a path having high input impedance and a path having substantially lower input impedance. The difference in magnitude between the resulting two signals is amplified by the circuit to more accurately detect changes in the patient's thoracic impedance and ventilation, and incidence of sleep apnea in the absence of ventilation. The sensed EKG signal may be transmitted through two separate paths, of high and low impedance respectively, to acquire the two signals of different magnitude for differential amplification. Alternatively, and preferably, the sensed signal is continuously switched, rapidly and alternately, from the high input impedance of the processing circuit to the low input impedance provided by a shunt load in the processing path. The switching (i.e., alternation) rate or frequency should be high enough to assure sufficient resolution for detecting depolarization and repolarization of the heart, and, more significantly, for detecting ventilation. As a result, a continuous sequence of pairs of electrical signals obtained from high and low input impedance paths and resulting different magnitude is provided for further differential signal processing. The thoracic impedance and ventilatory status of the patient are determined from continuous differential amplification of the signal pair sequences. Among other clear advantages of the invention in detecting individual episodes of sleep apnea, the processing of energy generated by the heart alone substantially reduces drain on the battery simplifies the electronic design of the implanted device, to allow reduction in battery size and lengthening of device lifetime, compared to previous techniques.

Upon detecting an episode and the form of sleep apnea (if either CSA or CSR) from the respiratory pattern, phrenic nerve stimulation is delivered in a conventional manner as the therapy to terminate the episode and restore patient ventilation and halt the apnea episode. This may be accomplished, for example, by applying regular bursts of electrical stimulation directly to the phrenic nerves or a phrenic nerve from an electrical stimulator of the implanted device, to cause contraction of the diaphragm with each burst and concomitant expansion of the lungs, and, during the interval between bursts, to allow relaxation of the diaphragm for contraction of the lungs. The stimulation pattern may be adjusted to control the pace of the contractions, so as to achieve the desired diaphragmatic pacing. In this case, the monitoring of ventilation by the device serves and functions in a closed loop system. In addition, or if therapy is ineffective to terminate an episode of sleep apnea, conventional warning signals can be generated, as by vibratory or tickling signals from the implanted device or alarms from an external bedside monitor activated by telemetry, to awaken the patient so as to enable restoration of normal or near normal respiration.

In the case of detection of an episode of OSA, electrical stimulation may be delivered, for example, to muscle adjacent or near the soft palate, rather than to the phrenic nerves, so as to increase muscle tone in the region of the palate sufficiently to move the palate and expand and reopen the blocked respiration airway, and thereby enable the still-sleeping patient to resume normal breathing.

Information regarding form and number of sleep apnea episodes, false positives, nature of therapy delivered (or not delivered in any particular instance) and other diagnostic insight may be stored in cache memory of the implanted device, to be retrievable on command and through telemetry for review and evaluation by the attending physician. Depending on evaluation of this information and condition of the patient, the physician may make limited changes in the programming of the device to achieve desired prescribed results.

BRIEF DESCRIPTION OF THE DRAWINGS

The above and other aims, objectives, aspects, features and advantages of the invention will be better understood from a consideration of the following detailed description of the best mode contemplated for practicing the invention, taken with reference to certain preferred implementations and methods, and the accompanying drawings in which:

FIG. 1A-1D are schematic diagrams of an electrical circuit or system in which a patient's heart is represented by an internal resistance, useful for explaining basic principles of the invention;

FIG. 3 illustrates various situations in which the internal resistance of a patient's heart is represented in parts A, B, C and D not as one single value, but by plural individual impedances;

Figure 2B:
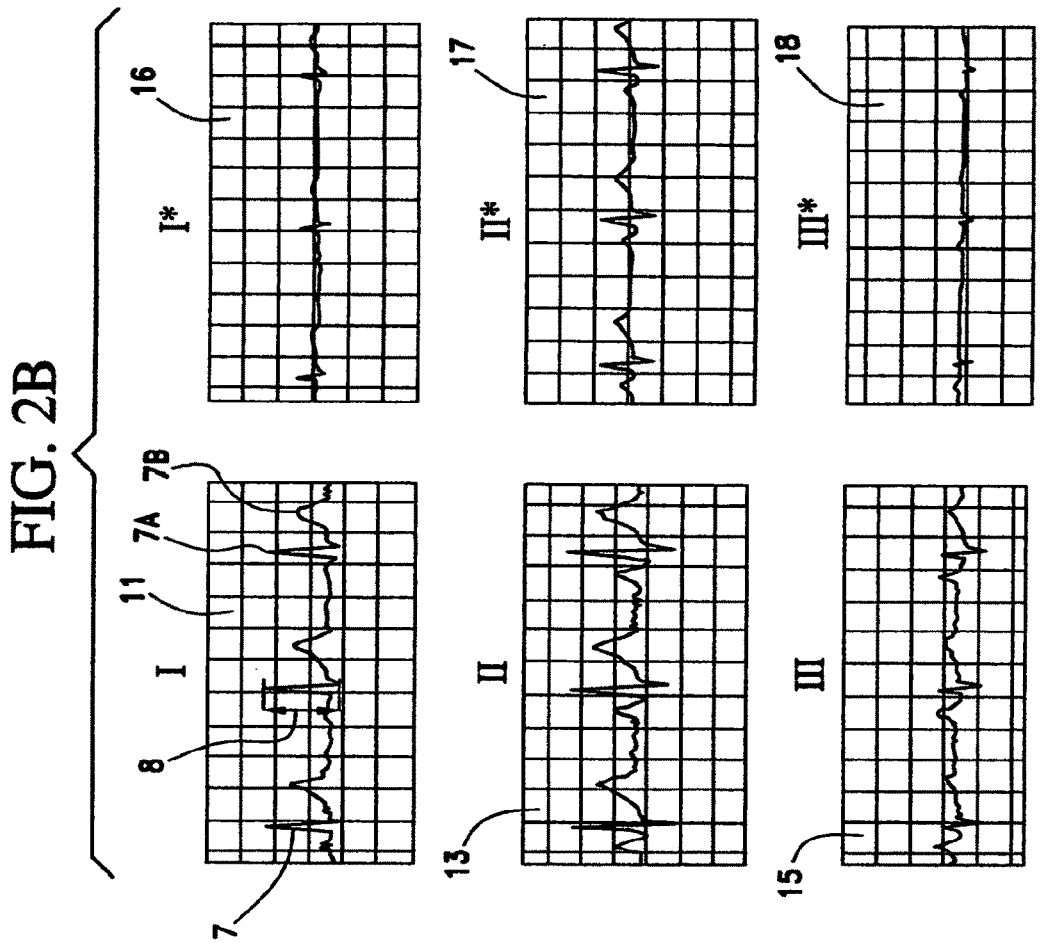
FIG. 2 applies the concepts discussed with reference to FIG. 1, to the principle of different EKG vectors, FIG. 2A illustrating EKG vectors measured for a patient, and FIG. 2B illustrating the EKG tracings for different placements of EKG electrodes.

DETAILED DESCRIPTION OF THE PRESENTLY CONTEMPLATED BEST MODE OF PRACTICING THE INVENTION

As is known, a patient's EKG can be derived from the skin surface of the patient, and represents a voltage (a cardiac signal) generated by the heart. This voltage may be derived by means of electrodes which are adhered to the skin of the patient. Use may be made of different leads, with bipolar electrodes for example between the right arm and the left arm, in the way that the resulting voltage change between these two electrodes represents the main vector of the heart in projection to those leads. Therefore, the amplitude is a measurement of the voltage generated by the heart and the vector. The input impedance of an external EKG machine is standard in a range between 1-10 megohms. This means that the input impedance and resistance of such an amplifier is very high and therefore no current is shunting through the machine and the voltage always represents the maximum voltage generated from the energy source, namely the heart. Differences in voltages with the current EKG measurement result from different vectors that project two different leads on the surface of a patient.

The same holds true for voltages detected with implantable devices from leads that are situated within the heart or within the thorax or even implantable devices that have EKG electrodes outside the thorax, such as EKG loop recorders or devices that are suitable for monitoring the EKG and congestive heart failure from electrodes that are situated outside the thoracic cage as described by Alt et al in the aforementioned related patent application U.S. Ser. No. 10/155,771.

The underlying principle may be summarized, for exemplary purposes, from experiments conducted by the applicants. The measurements that resulted from placement of standard EKG I, II, and III leads on the patient were recorded in the presence and absence of an external load. The amplitude of the EKG signal that corresponds to the measured voltage is a function of the impedance of the EKG amplifier.

The theory is that the heart acts as a battery. A battery fails when its internal resistance has increased to a level at which the battery can no longer supply a useful amount of power to an external load. That same principle applies to the measurement of electrical energy generated by the heart. That is, if several loads are applied to the measurement device, which, for example, may be an implantable cardiac pacemaker, a defibrillator, a device for monitoring the occurrence of heart failure, a nerve or muscle stimulation device, or a diagnostic device for monitoring the physical condition of a patient, the same phenomena can be used to calculate the internal impedance at the site of measurement. Preferably, the calculation or determination is of the thoracic, intrathoracic, cardiac or intracardiac impedance or of local impedance and/or its relative changes with time for a given patient.

According to an important aspect of the invention, a method of evaluating the cardio-circulatory condition and ventilatory status of a patient includes determining the patient's intracardiac, intrathoracic or thoracic impedance based on information from electrical signals derived solely from electrical energy generated by the patient's own heart and delivered as the sole input to signal monitoring or detection circuitry. This impedance information may be used for a variety of different medical purposes, which may be diagnostic and/or therapeutic in nature. For example, the device may be implanted subcutaneously to monitor the patient's EKG, and to detect changes in the thoracic impedance based on differential signal processing of the EKG. Then, information concerning the impedance changes may be applied within the device to determine the cardio-pulmonary status of the patient. In circumstances where the patient is suffering from sleep apnea, the device is adapted to monitor and evaluate the patient's ventilatory status, as a basis for enabling detection of the onset of an episode of sleep apnea.

Information about the cardiac function of the patient may be obtained using a method in which electrical signal information from an EKG derived from depolarization and repolarization of the patient's heart, representing systole and diastole, accordingly for different phases of the heart represented by the EKG, is continuously processed using as its basis, the electrical signals generated by the patient's own heart. On the other hand, the impedance of the patient's heart may be analyzed with systole from a single point close to the T-Wave of the EKG signal, and information on the diastolic status of the heart may be derived from a discrete impedance signal at the R-Wave of the EKG signal. Then, a comparison between systole and diastole may be used to ascertain indirectly cardiac stroke volume and the cardio-pulmonary status of the patient.

A device for evaluating the ventilatory condition of a patient is implemented with means for determining the patient's thoracic impedance and changes in that impedance based on information derived from the electrical energy generated by the patient's heart. And the desired information may be obtained by extremely simple means so that the changes or additions required to achieve these benefits with even currently available devices can be minimal, such as including surface mounted electrodes on the device for monitoring the patient's EKG in subcutaneously implanted devices.

Referring to FIGS. 1-12, the basic underlying method and device are described in terms of a diagnostic and/or therapeutic technique to enhance the specificity of a body-implantable device implemented as a stimulator or neurostimulator.

Throughout the views of the drawings, identical reference numbers indicate identical structures, elements or items. The Figures are not intended to represent the actual or relative sizes of devices, but rather, to provide an understanding of the principles on which the methods and devices are based.

FIGS. 1A-1D are simplified schematic diagrams of an electrical circuit or system in which the heart of a patient 1 is represented by an internal resistance ($R_{internal}$) 2, at least in parts 1A and 1B. In principle, $R_{internal}$ is the sum of many individual resistances or impedances consisting of myocardial tissue, fibrous connective tissue in the heart, pericardium, blood within the heart, fluids within the intracellular spaces, and the surrounding environment of connective tissue atria, pulmonary structures, venous structures, and lung tissue, which may be characterized variously herein as the cardiac impedance, intracardiac impedance, thoracic impedance or intrathoracic impedance. The multiplicity of cells within the heart depolarize, and this depolarization (systole) creates an electrical force which threads through the heart with a certain vector. This initial electrical source represented in the circuit schematic of the Figures as a voltage source E (3) has a magnitude that can be measured between electrodes at points A (4) and B (5). The latter two points may constitute the sites of electrodes of an external measuring instrument or EKG amplifier.

Virtually the same voltage as the original source voltage E 3 will be present and remain so, if the impedance between measuring points 4 and 5 has a magnitude of several megohms. This is because under that condition little or no current is flowing between those points. In principle, this maximum voltage is present, for example, at the input amplifier of an implantable neurostimulator, which may typically have an impedance of several hundred kilohms or megohms; and the same is true of other implantable diagnostic or therapeutic devices, such as devices that measure the patient's EKG. For example, external EKG strip chart recorders or EKG monitors have an impedance of 1 megohm or more, thereby allowing them to detect the maximum voltage present between points of the body at which their electrodes are attached or located.

In FIG. 1B the schematic shows a heart 1, in circuit with an internal resistance 2, a source voltage 3 that is detected between electrode points or sites 4 and 5, corresponding to what has been described above for FIG. 1A. However, in this case an additional external resistance of magnitude $R_{Load}$ 6 is connected in circuit between electrode points 4 and 5. If the magnitude of the resistance of load 6 is considerably lower than the input impedance between 4 and 5 represented by, say, the virtual open circuit impedance of an amplifier, discussed for the circuit of FIG. 1A, considerable current will be shunted through this lower resistance. As in the case of a failing battery, then, the initial full voltage E (3) will not be detected since, by Ohm's Law (U=IR), a drop in voltage will be observed with decreased R.

This example is carried forward in FIGS. 1C and 1D. In each of those Figures, the heart 1 generates a certain EKG signal 7 between measuring points 4 and 5, which has a certain amplitude 8. In FIG. 1D, the connection of an input amplifier 8 with a relatively low resistance $R_{Load}$ 6 across points A and B results in an EKG signal 7 having an amplitude considerably lower than that in the case of the much higher, virtually open circuit resistance across A and B in FIG. 1C.

In principle this observation can be compared to a battery. When a battery fails it is typically because its internal resistance has increased to a level that no longer supports the supply of a useful amount of electrical energy to an external load. If one measures the voltage V of a failing battery which is disconnected, it is usually found that the battery has a nearly normal voltage because a conventional voltmeter used to perform the measurement has an input resistance much higher than the internal resistance of the battery. If, however, the failing battery is connected to a low external resistance such as load 6 in FIG. 1B, the terminal voltage U of the battery drops precipitously. This can be interpreted as the battery dropping most if its source voltage across its own internal resistance, so little or no voltage is available for external services. For example, an ideal battery with 0 internal resistance or infinite internal conductance and a voltage E of 12 volts, when supplying power to an external load having a resistance of 1 ohm, will produce a current of I=12 amps and a power of E×I=144 watts. If the battery has an internal resistance of 2 ohm, or an internal conductance as low as 0.5 siemens, then with this load, the terminal voltage U of the battery will drop to 4 volts. The output current of this failing battery will drop to $I=U/R_{Load}$ which is 4 amps, and the output power is 16 watts.

The same principle holds for conventional electrocardiography along the main electrical excitation vector. Since an EKG measurement is detected with high input impedance, this conventional measurement gives no insight into the electrical power of the source, in this case the heart of the patient. Furthermore, the absolute voltage of EKG signals is not a valuable indicator of various pathological situations. Indeed, despite great diversity of cardiac diseases it is common clinical experience that individual variability and the amplitude of the EKG wave as detected from state of the art EKG amplifiers is not indicative of any kind of disease. The voltage of a conventional EKG is reduced only in very few clinical situations when large electrical shunts are present, such as a pericardial effusion which constitutes a large conductor around the heart that shunts the electrical energy with low intrinsic resistance.

The terminal voltage U in FIG. 1B (which represents the R wave amplitude 8, represented in FIG. 1C by QRS-complex 7) should drop by $E-(R_{internal} \times I)$, where $I=U/R_{Load}$. The internal resistance $R_{internal}$ 2 can be calculated by the equation $R_{internal}=(V-U)/(U/R_{Load})$, where V is the voltage between electrode points 4 and 5 which is disconnected from the load in FIGS. 1A and U is the terminal voltage between 4 and 5, across which the electrical load $R_{Load}$ 6 is connected. Based on $R_{internal}$, the internal electrical conductance $S_{internal}$ of the heart can also be calculated by the equation:

$$S_{internal} = 1/R_{internal}, \text{ in siemens.}$$

Figure 2A:
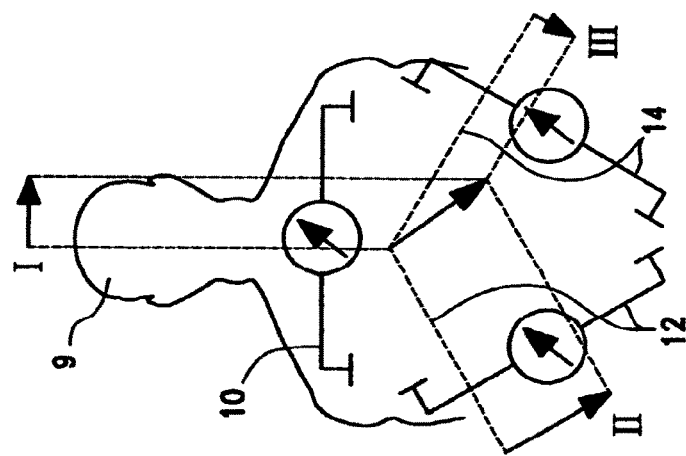

These equations are applied in practice in FIG. 2, according to the principle of different EKG vectors. FIG. 2A represents a patient 9 in which EKG lead I 10 is represented by electrodes to the patient's right and left arms, with voltage measurements shown in EKG tracing 11 (FIG. 2B). Electrode detection lead/electrodes II 12 produces the tracing 13, and the voltage detected between the electrodes of lead III 14 is shown in the tracing 15 for lead III. Tracings 11, 13, and 15, then, represent the EKG signal obtained for the respective vector projections of the leads 10, 12 and 14. If an external load is now connected in parallel with the input impedance of the EKG amplifier, a voltage drop will be observed for the same patient as shown by tracings 16 (for lead I), 17 (for lead II), and 18 (for lead III), because part of the energy delivered from the patient's heart is shunted through the additional external load.

FIG. 3 illustrates various situations in which the internal resistance $R_{internal}$ of the heart is represented not as one single value, but by plural individual impedances. In FIG. 3A, the internal resistance $R_{heart}$ of the heart 19 is represented by the structural resistance of the heart made up of cells, connective tissue, and primarily solids, and a variable component of resistance $R_{inspiration}$ (or $R_{insp}$) 20 is primarily represented by the filling of the heart with blood. Since blood has a specific impedance of roughly 50 ohms per centimeter (cm), while the specific impedance of heart 19 is 400 ohms per cm, there exists a great influence on the total impedance of the heart, because these two components are in parallel. The internal voltage source 3 in FIG. 3A detected between electrode points 4 and 5 represents a voltage $V_1$ (22) that equals primarily E 3 if the input impedance between 4 and 5 is sufficiently high that all of the voltage E drop occurs between 4 and 5.

If, however, an additional external load $R_{load}$ 6 of roughly 1 kilohm or less is applied as shown in FIG. 3B, then the voltage between 4 and 5 drops to a voltage U1 (23) which, as earlier described, is lower than the voltage E 22. FIG. 3C illustrates the situation in which a variation now occurs in internal resistance 21, representing the resistance with expiration ($R_{expiration}$ or $R_{exp}$). The total voltage to be detected $V_2$ 24 is now primarily composed of the parallel resistances of $R_{heart}$ 19 and $R_{exp}$ 21. A variation between $R_{insp}$ 20 and $R_{exp}$ 21 will not affect the resulting voltages, $V_2$ 24 or $V_1$ 22, since the input impedance between electrodes 4 and 5 is sufficiently high to avoid further voltage shunting and voltage drop. However, as shown in FIG. 3D, the external load 6 will affect voltage $U_2$ 25 with a variation in internal impedance 21 during expiration, compared to impedance component 20 during inspiration. Thus, if an external load 6 of sufficient load resistance, such as 1 kilohm, is applied to a primarily high input impedance amplifier, variations in internal total resistance build up from $R_{heart}$ 19 and $R_{respiration}$ 20 or 21 have a much greater effect on voltage $U_1$ 23 with inspiration and $U_2$ 25 with expiration. In principle, for this condition it can be said that $R_{inspiration}$ is not identical with $R_{expiration}$ and therefore, $U_1$ 23 is different from $U_2$ 25. It follows that $U_1$ equals the delta of $U_2$, and this represents more or less the impedance factor of respiration, the term "impedance factor" meaning the quotient of impedances 19 and 20 in FIG. 3B compared to the impedances 19 and 21 in FIG. 3D.

Figure 4:
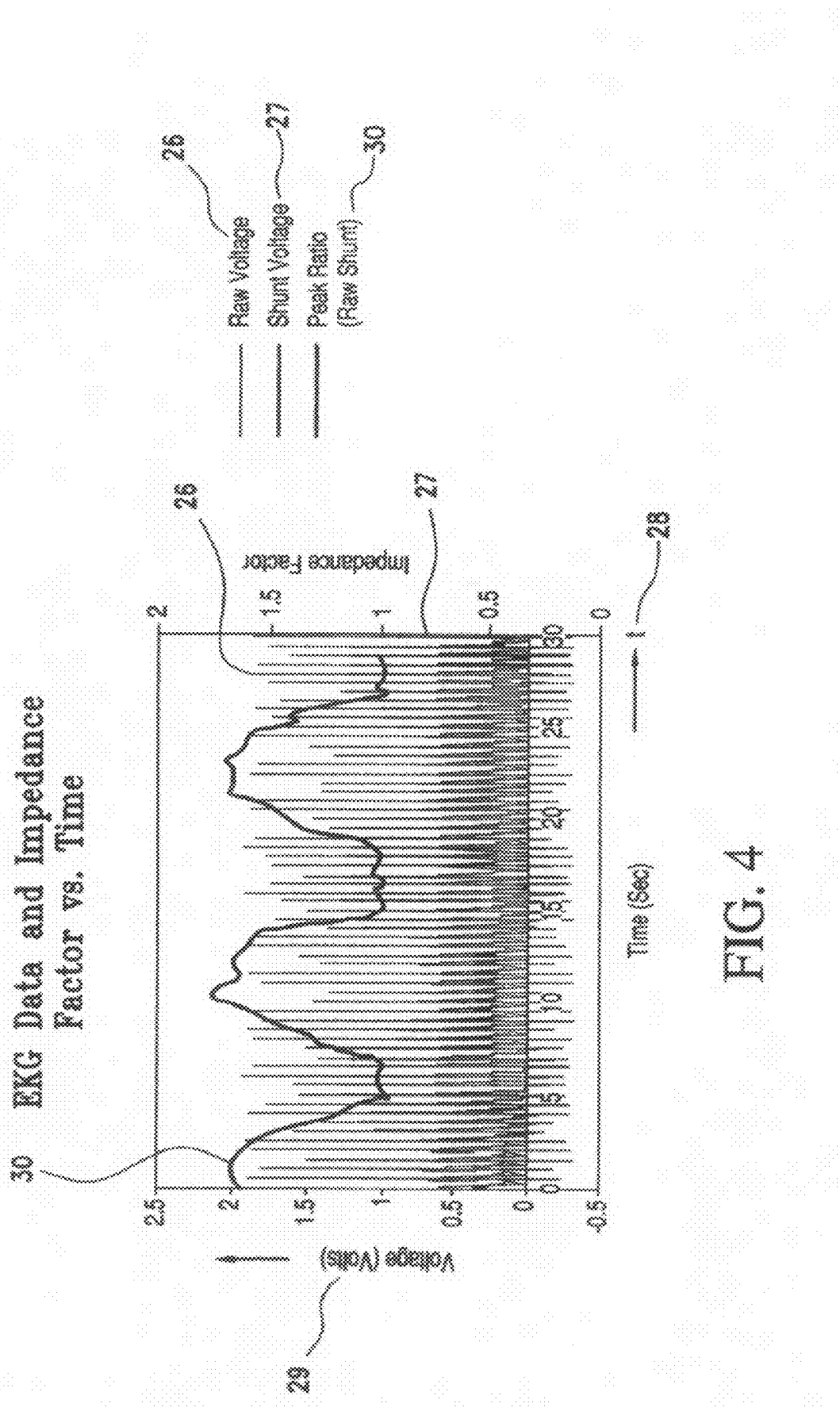
FIG. 4 is a graph of EKG data and impedance factor versus time that illustrates results from measurements taken with an intracardiac electrode.

FIG. 4 is a graph of EKG data and impedance factor versus time that illustrates results from measurements taken with an intracardiac electrode. A bipolar conventional pacemaker electrode was implanted in the heart and measurements were taken between the electrode tip in connection with the myocardium and a ring located roughly 1 cm behind the electrode tip. These sites can be considered as electrode points 4 and 5 in the Figures described thus far, and a linear high quality amplifier was connected between these two sites. The signal processing was performed in such a way that one signal represented in FIG. 4 as raw voltage 26 represented by the higher bars in the graph was compared to a shunt voltage 27 represented by the smaller bars. To detect the shunt voltage from the same electrode site 4 and 5 by a special program, the input impedance was shunted by a resistance of one kilohm. In FIG. 4 the time axis (abscissa) 28 shows increments of time in seconds and the voltage axis (left ordinate) 29 shows increments of the detected voltage of the two signals raw voltage 26 and shunt voltage 27. The curve 30 represents the quotient between voltage 26 and voltage 27 (i.e., their impedance factor, measured along lines parallel to the right ordinate) or in other words, the quotient of the impedances that change with respiration.

As is clearly seen in the graph, the ratio of the peak signal between raw voltage 26 and shunt voltage 27 represented by curve 30 correlates with the respiration, which was set to 5.5 cycles per minute. The time interval for one respiratory cycle is 11 seconds in this example, which actually represents a ventilation rate of 5.5 cycles per minute.

Various aspects of the continuous EKG signal can be used to derive measurements of impedance factor in FIG. 4, to discern or determine the cardio-pulmonary or ventilatory status of the patient using a bipolar conventional electrode implanted in the body for monitoring purposes. Either a continuous line can be averaged if a sufficiently high digitization rate is applied, or, to simplify measurements and procedures, and also to facilitate data handling and power consumption in an implantable device, only certain aspects of the EKG signal need be taken. For example, the latter aspects may be those represented previously herein in EKG signal 7 with amplitude 8, so it is feasible to use only the peak 7A of the R Wave or to take other aspects such as only or additionally the T Wave peak 7B of the EKG signal 7 illustrated in FIG. 2B. In the example shown in FIG. 4, the peak of the R Wave was applied. From the latter Figure, it is clear that considerable variation occurs in the quotient represented by curve 30 (the impedance factor) between inspiration and expiration, which corresponds to the ventilatory cycle rate and its amplitude.

Figure 5:
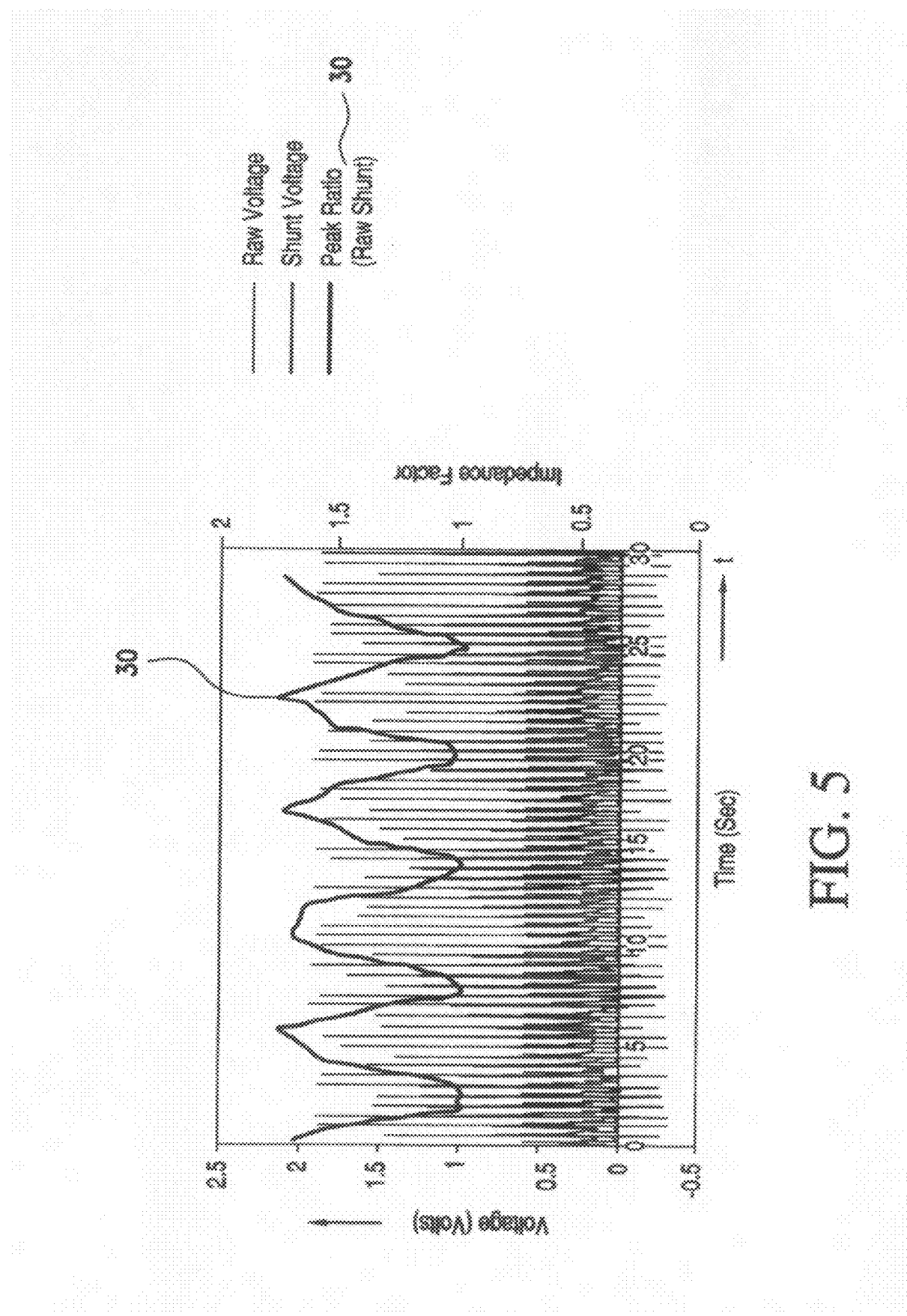
FIGS. 5 and 6 are graphs of EKG data and impedance factor vs. time corresponding to FIG. 4, except for changes (respective increases) in the respiratory rate.
Figure 6:
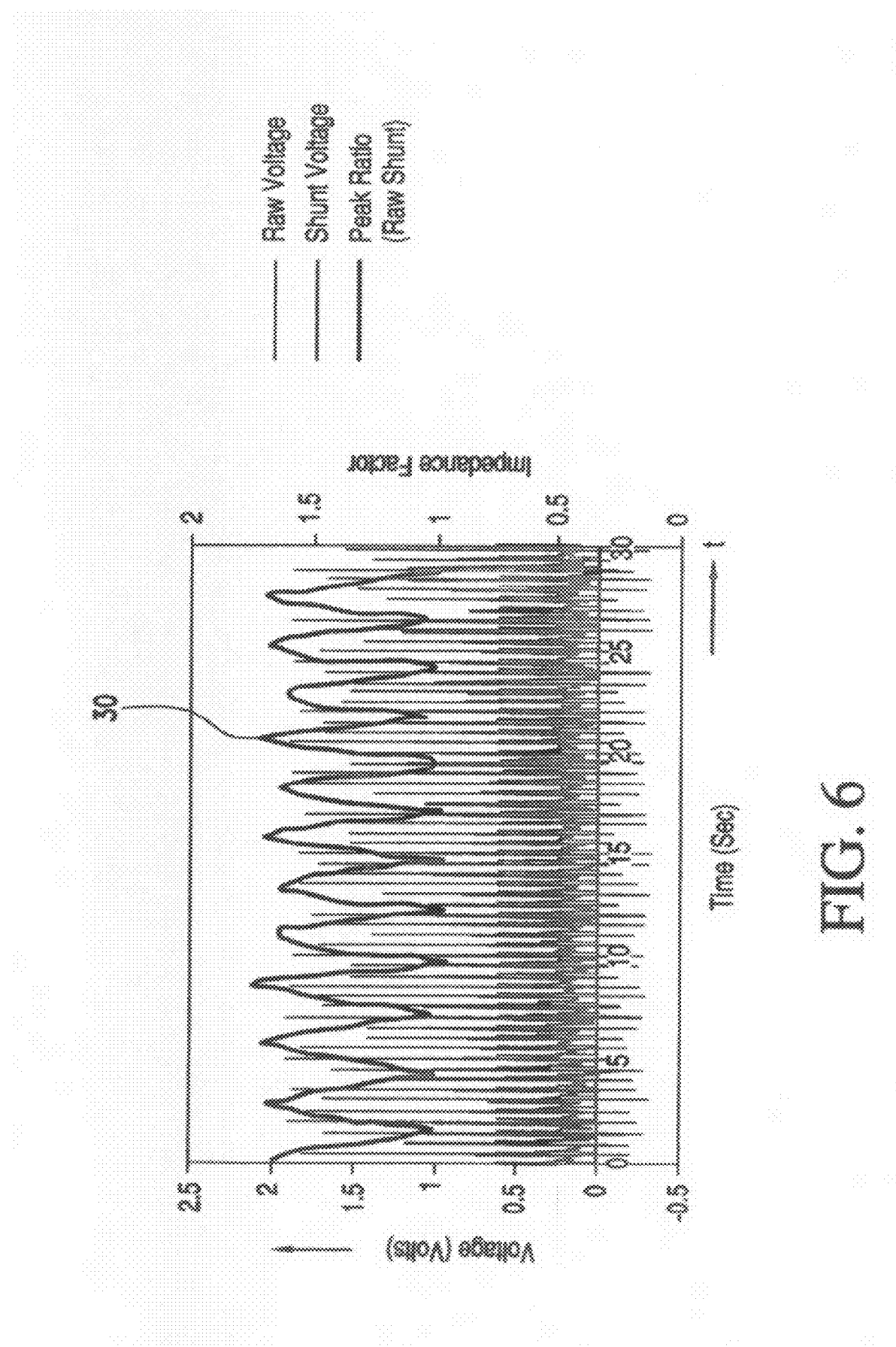

FIGS. 5 and 6 are graphs illustrating the same data setting and the same parameters as in FIG. 4; however, the respiratory rate was changed in FIG. 5 to 10 cycles, and in FIG. 6 to 20 cycles per minute. This change in frequency is clearly shown in the latter two Figures, being represented by peak ratio 30.

Figure 7:
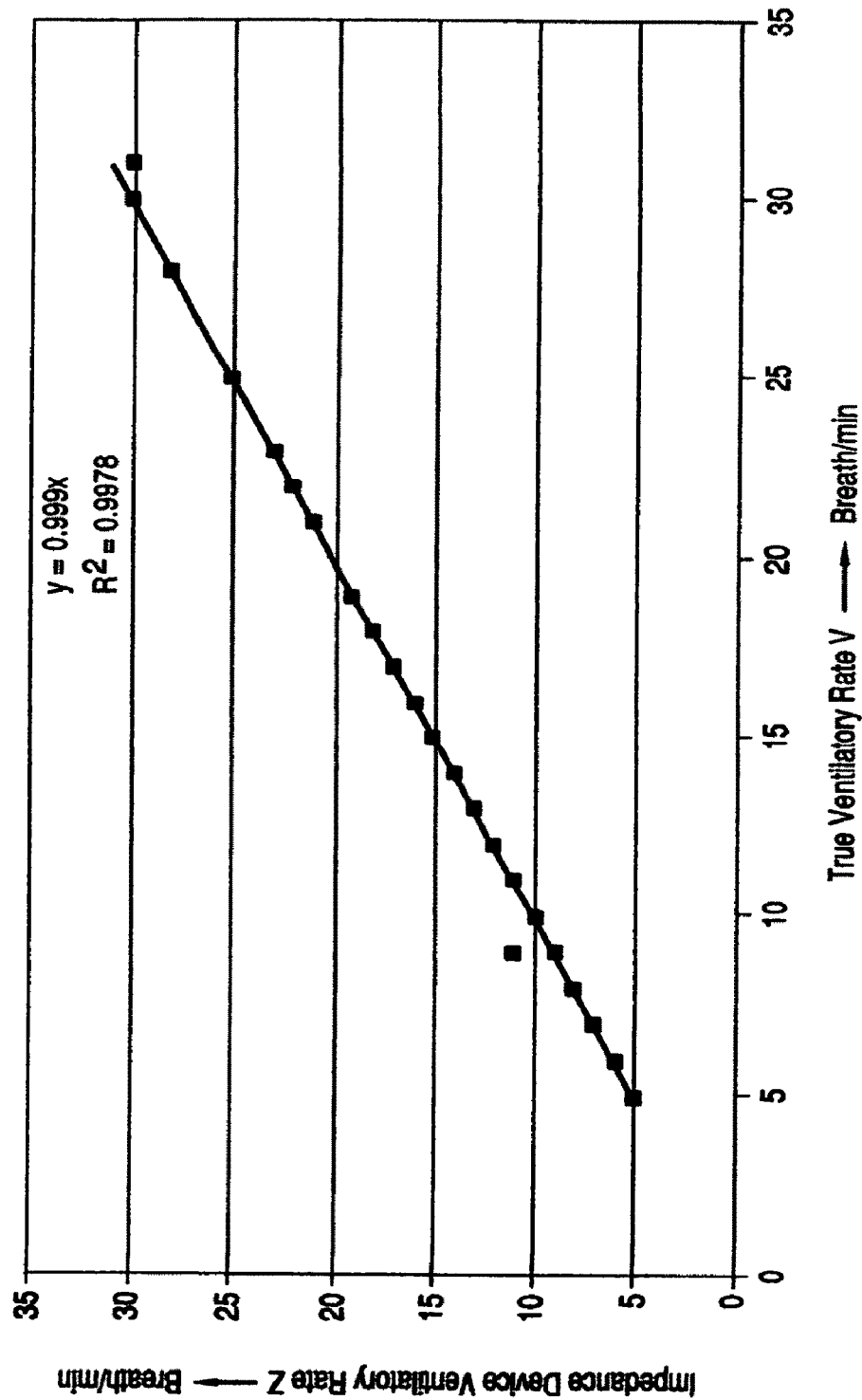
FIG. 7 is a graph that summarizes and compares the measurements of impedance derived ventilatory rate obtained using two different methods.

In the graph of FIG. 7, it is seen that a nearly 1:1 correlation exists between the true ventilatory rate V along the abscissa and the impedance factor (determined in accordance with the methods described earlier herein) derived ventilatory rate Z along the ordinate, for a given patient. This emphasizes that ventilation can be detected, in terms of frequency of breaths, from the impedance derived signal in which the heart serves as the power source for the impedance calculation.

Figure 8:
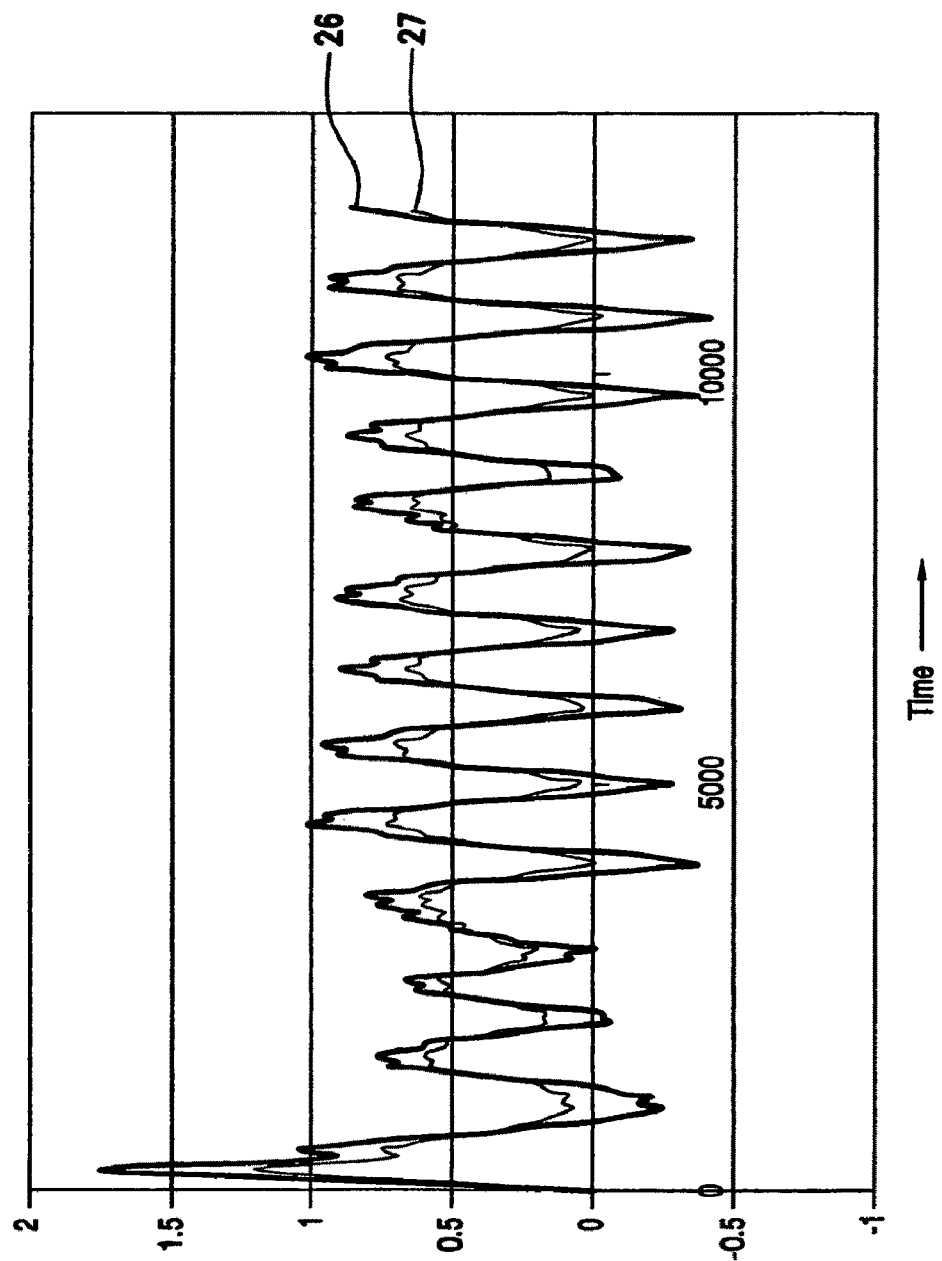
FIG. 8 is a graph that depicts a preferred application of the signal processing means, with relative signal amplitudes over time.

An application of the signal processing is depicted in FIG. 8, in which the relative signal amplitudes of the raw voltage 26 and the shunt voltage 27 (see FIG. 4 also) are indicated respectively by a higher amplitude and a lower amplitude. Signal 26 was detected from an input impedance exceeding 1 megohm, whereas signal 27 was detected from the reduced shunted input impedance of 0.5 kilohm), both signals having been smoothed by passage through a low pass filter during signal processing. A respiration rate of no more than 50 breaths per minute can be expected for most patients, so a low pass filter of about 1.5 Hz will allow detection of that rate. The difference in amplitude between signals 26 and 27, as well as the respiratory cycle rate, is evident from the Figure.

Figure 9:
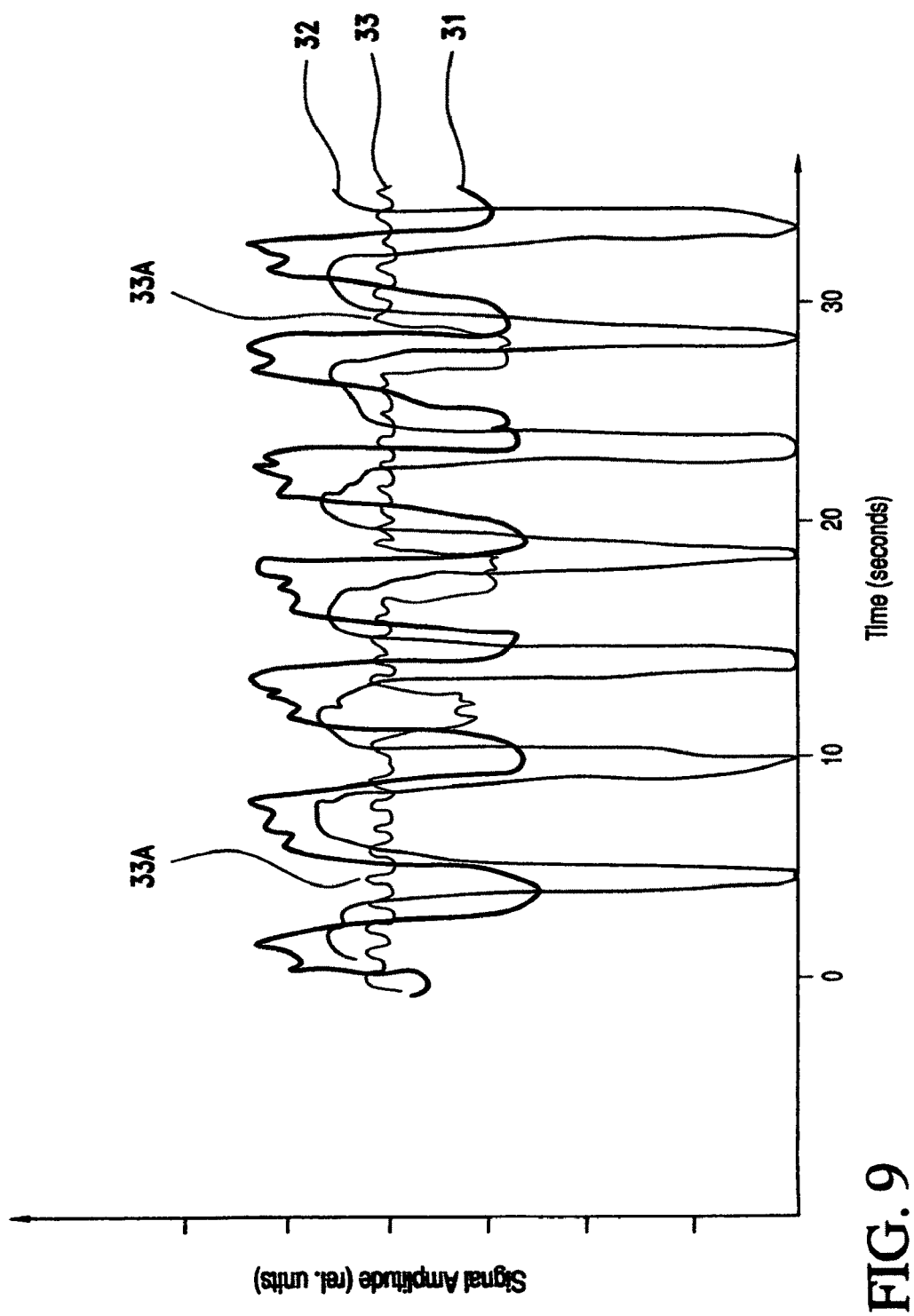
FIG. 9 is a graph that represents the quotient of raw voltage and shunt voltage with different depth and modes of breathing.

FIG. 9 is a graph representing the quotient of raw voltage and shunt voltage with different depths or amplitudes and modes of breathing. The graph illustrates it is feasible to detect respiratory rate, affected by a volume change in the filling of the heart with blood, and also to detect a relative change in amplitude following different tidal volumes. Wave 31 depicts a signal derived from the quotient of high input impedance exceeding 1 megohm and low impedance of 1 kilohm with external artificial ventilation of an individual with a tidal volume of 300 ml per breath. Wave 32 depicts the same for a tidal volume of 850 ml per breath, and wave 33 depicts the impedance quotient with spontaneous breathing at a considerably lower rate. In addition to showing breathing or ventilation, the graph depicts the cardiac component 33A that indirectly reflects stroke volume with systole and diastole. The latter may be obtained, for example, from the observation that depolarization occurs as represented by the peak of the R wave 7A (FIG. 2B) and repolarization occurs at the peak of the T wave 7B, with the mechanical contraction occurring slightly after the peak of the R wave. At that point, the intracardiac impedance (or thoracic impedance) allows determining the extent of filling of the heart with blood, from which to assess the ventilation status of the patient.

Figure 10:
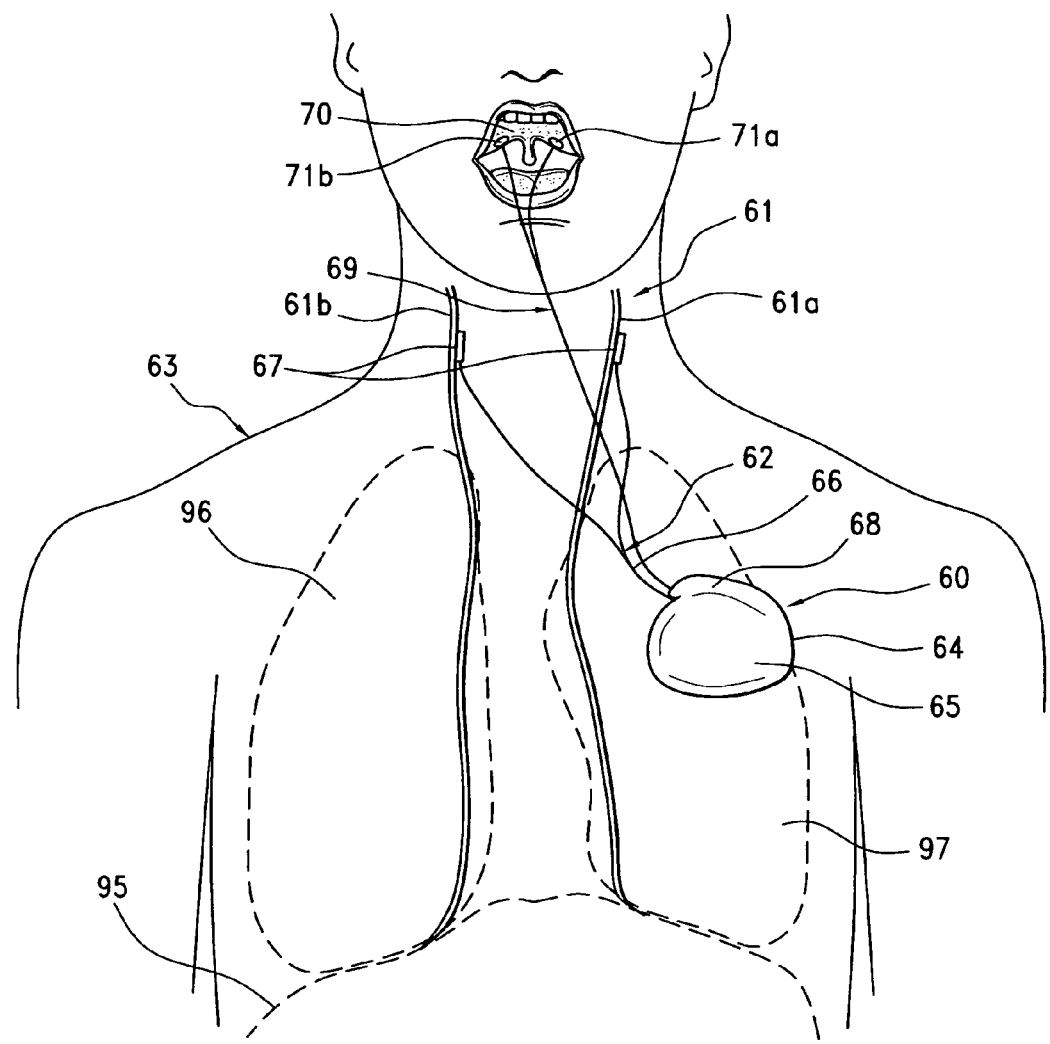
FIG. 10 is a simplified diagram of a sleep apnea detection/therapeutic delivery system including a device and associated EKG signal sensing and pulse stimuli delivery lead-electrode system implanted in the body of a patient for phrenic nerve stimulation or soft palate muscle stimulation depending on type or form of the sleep apnea.

FIG. 10 is a simplified diagram of a sleep apnea detection/ therapeutic delivery system including device 60 implemented to perform the method of the invention, and associated EKG signal sensing and pulse stimuli delivery lead-electrode system 62 implanted in the body 63 of a patient suffering from a sleep apnea disorder. The manner of an exemplary physiological accommodation of the implanted device and associated lead-electrode systems is illustrated for signal sensing and either or both of phrenic nerve stimulation (PNS) in the case of CSR or CSA and soft palate muscle stimulation in the case of OSA, depending on which of these types of sleep apnea is detected. Device 60 includes a housing 64 (typically referred to in the art as a "can" or "case") for a stimulus generator 65 (illustrated in block diagram form in FIG. 11A, and described in connection therewith). The case is of conventional composition for body implantation and is suitably sized (dictated primarily by its internal battery) for insertion into a surgically-formed pocket just below the skin, typically in a pectoral region of the patient, although other locations in the thorax or abdomen may be used. An implanted insulated lead body 66 has an internal electrically conductive lead array with its proximal end electrically coupled to generator 65 through connectors in the device header 68, and its distal end appropriately connected to respective ones of a pair of electrode arrays 67. At least one of the electrodes of each array 67 is positioned to engage (i.e., to be operatively coupled with) the patient's phrenic nerve 61 for use in treating CSA or CSR by delivering stimulating pulses or pulse bursts in a predetermined pattern and rate to the nerve when therapy is determined to be necessary.

The phrenic nerve stems from the cervical region (primarily $C_4$) of the spine and functions primarily to carry motor impulses to muscles of the diaphragm to supply movement thereto (specifically, contraction), as well as to carry sensory information from parts of the lungs and pericardium of the heart. The nerve 61 is split into left and right side nerves 61a, 61b, that follow different, somewhat parallel paths along the left and right lungs, respectively. Preferably, electrodes or arrays are operatively coupled to both the left and right nerves as shown, although alternatively, only one side of the phrenic nerve may be so outfitted. In any event, the stimulation electrodes are positioned in a location relatively remote from the heart to avoid deleterious interference with the intrinsic electrical excitation of the heart.

According to an aspect of the invention, the EKG signal to be processed by device 60 in performance of the method is sensed directly from at least one of the same electrodes of the respective array 67 as is used for stimulation of the phrenic nerve. For example, if the stimulator is used exclusively in a synchronous burst mode for phrenic nerve stimulation, it is preferable that the same nerve electrode of the respective array be used in both sensing and stimulation. Preferably, bipolar sensing is performed. Among suitable arrangements for sensing, a separate lead within lead body 66 may be connected to two electrodes at the site of or nearby the phrenic nerve, or through electrodes in the immediate vicinity of the phrenic nerve and engaging the metal case 64 of implanted device 60 as a third pole, or through the case alone and respective surface-mounted electrodes on the case (and insulated therefrom), electrodes on the header 68 or a combination of different electrode points on the case, on the header and/or on the electrode body.

For some techniques, sensing and stimulation should not be performed from the same nerve electrode(s), so as to avoid missing a sense event while nerve stimulation is being delivered, but instead may require a distinct separate sensing electrode. Such a separate electrode for sensing may be incorporated as an integral part of the stimulus generator 65, either on the case 64 or on the header 68; or a separate lead may be used with a sense tip positioned away from the stimulating electrode. Alternatively, a ring sense electrode located around the lead body some distance from the electrode(s) used for stimulation, may be utilized on its own lead.

Similar considerations are involved in situations where treatment is used to terminate an episode of OSA, except that a separate lead-electrode system 69 is implanted for electrical or operative coupling of electrodes 71a, 71b to muscle adjacent or nearby either side of the patient's soft palate 70. The soft palate is movable, consisting of soft tissue (lacking bone) in the form of muscle fibers sheathed in mucous membrane, that among other things closes off the nasal passages and the airway during swallowing. For OSA therapy, the stimulating pulses are applied from stimulus generator 65 solely to the stimulating electrode(s) of electrode array 69 at the muscle site(s), to improve muscle toning during sleep so as to move the soft palate from its position of obstruction and re-open the respiratory airway.

Figure 11A:
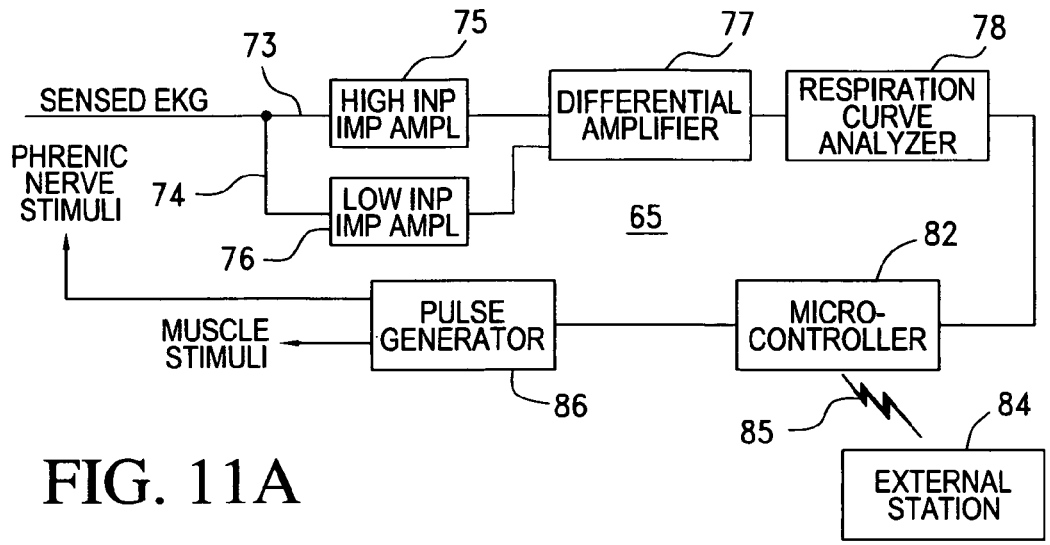
FIG. 11A is a simplified block and flow diagram depicting principles of the method and signal processing of the present invention in a system for ventilatory status-based phrenic nerve stimulation or soft palate muscle stimulation to terminate an episode of CSA/CSR or OSA sleep apnea, respectively.

Referring now to FIG. 11A, a simplified block and flow diagram is used to illustrate certain principal aspects of the invention. The sensed EKG signal at sense electrodes of respective electrode arrays 67 is applied to the stimulus generator 65 of implanted device 60. This signal is processed as the sole input through an initial differential signal processing circuit comprising a pair of signal paths 73, 74 to pass through a high input impedance amplifier 75 and a considerably lower input impedance amplifier 76, respectively. For example, the input impedance presented to the EKG signal on path 73 may have a magnitude of 1.0 megohm, and the input impedance of path 74 may have a magnitude of 0.5 to 1.0 kilohm. Owing to the different input impedances of the two paths, the output signals of amplifiers 75 and 76 are of different magnitudes. These two signals are applied to a differential amplifier 77, and its output signal represents detected changes in the patient's thoracic impedance. The latter signal is applied to a respiration curve analyzer 78, for determination of the ventilation status of the patient as discussed in connection with the description of FIGS. 1-9. Significantly, and in contrast to prior art techniques, ventilation is detected, in terms of frequency of breaths (or the cyclical respiration curve), and in terms of depth of ventilation, from the impedance derived signal in which the heart serves as the power source for the impedance calculation. Thus, the method of the invention relies on sensing the EKG signal from electrical energy generated by the heart alone, continuously applying that signal to a differential processing circuit to obtain thoracic impedance changes, assessing those changes (contained in the output signal of a differential amplifier) in a respiration curve analyzer as being indicative of patient ventilation, and detecting absence of ventilation from the respiration curve analysis, which represents the possible onset of an individual incident or episode of sleep apnea at the output of the analyzer.

Figure 11B:
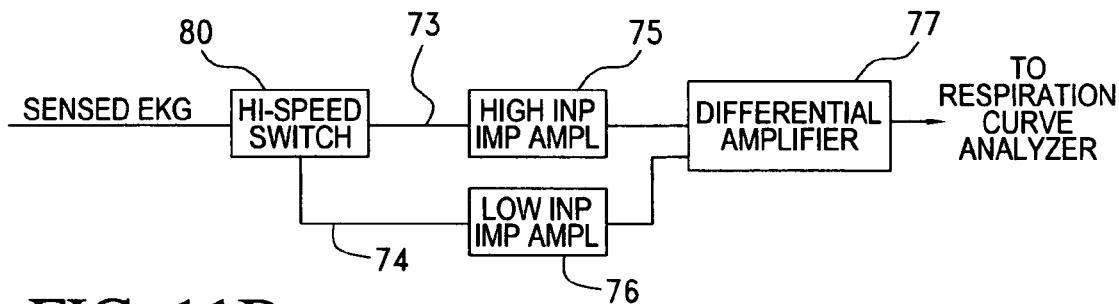
FIG. 11B illustrates a modification of a portion of the signal processing system of FIG. 11A.
Figure 12:
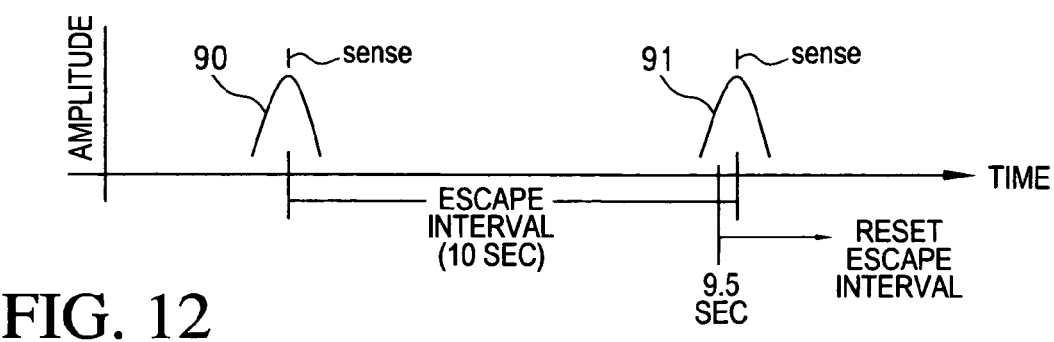
FIG. 12 is a respiratory cycle timing graph.

Preferably, as shown in FIG. 11B, the high and low impedance signals of different magnitude are obtained from the sensed EKG signal in a digitized format by continuously switching between the high and low input impedance paths to produce alternating or chopped successive pairs of the signals to be compared. This is achieved in an exemplary embodiment by shunting the sensed signal around the high input impedance amplifier 75 in signal path 73 and through the low input impedance amplifier 76 in signal path 74 at a frequency of, say, 1000 times per second, by means of high-speed or low-speed electronic switch 80 at the input to the two signal paths. Operation of the switch may be controlled by a microcontroller 82 of the device. Such processing improves the resolution and accuracy of the ultimate detection of patient ventilation. And the successive pairs of high and lower magnitude signals are differentially amplified to determine the changes in thoracic impedance of the changes, with subsequent analysis, for such detection.

In a conventional EKG input system, the impedance of the system consists of the transitional impedance of the electrode-heart interface. That is to say, it is a local contact impedance, which is a static impedance measured only through the high input impedance presented by the customary EKG measurement device or input portion thereof, typically one or two megohms. This arrangement is useful to determine the integrity of the lead-electrode system, e.g., whether a lead is fractured, or the reliability of contact between the electrode and the heart or the nerve in engagement with it. Inadequate insulation in the system is discerned because it produces a low impedance reading.

In contrast, in the system of the invention a dynamic change in impedance is detected or measured by using a high input impedance load as a baseline, and comparing the magnitude of that load to a substantially lower input impedance load with a considerable voltage drop. In the system of FIG. 11A, modified according to FIG. 11B, the chopped (as a result of the rapid switching by switch 80) replica of the sensed EKG signal may be input, alternatively, directly on path 73 to the differential amplifier 77, which has a high input impedance, without an intervening amplifier 75, although the configuration shown in FIG. 11B is preferred. These controlled rapidly alternating changes in input impedances are in parallel with the thoracic impedance as determined from the EKG signal, to enable detection of dynamic changes in the impedance. The availability of a dynamic impedance enables more accurate measurement and evaluation of patient ventilatory status. A significant additional advantage resides in the considerable reduction in drain on (and concomitant increase in longevity of) the battery of the implanted stimulus device compared to prior techniques, since the present invention relies on electrical energy generated by the heart itself. Moreover, an overall simplification of the electronics can be achieved using this method.

The thoracic impedance/ventilation parameters in digital form are inputted to a microcontroller 82 including a microprocessor, which, among other things, detects and determines the type of sleep apnea at onset of an episode, and controls the delivery of appropriate therapy, with accessible memory for programming and retrieval of stored data, as well as logic and timing circuitry, state machine circuitry, and input/output circuitry. The memory stores long term, short term, and derivatives of the information, including data reflecting ventilation, mean and maximum respiration, frequency of occurrence and length of respiratory pauses. Such data may be retrieved, and other information relevant to the condition of the patient may be programmed and re-programmed as necessary, by an attending physician at an output station 84 via telemetry 85. The microcontroller 82 and its associated logic and timing circuitry are implemented to control the output electrical stimulation format or regimen from a pulse generator 86 of stimulus generator 65. Preferably, therapy is delivered in a burst of electrical pulses formulated according to the thoracic impedance/ventilation factors, to stimulate the patient's right and left phrenic nerves 61b, 61a, respectively, in the case where the onset and form of an episode of CSA or CSR sleep apnea is detected.

But as noted above, the absence of ventilation is merely indicative of possible onset of an episode of sleep apnea. For a variety of reasons, including the need to conserve battery power of the implanted device 60, it is desirable to prevent the occurrence of false positives that would lead to unnecessary and undesirable PNS when, in fact, sleep apnea is not present. Accordingly, in the device and method of the invention, a rule is established (implemented by microcontroller 82 in conjunction with respiratory sleep analyzer 78) that cessation of patient breathing must have taken place for a predetermined sustained interval of time that may range from, say, 10 to 30 seconds, before it is deemed to be the onset of an actual episode of sleep apnea. To that end, the invention performs PNS from the implanted stimulus generator 65 only after the expiration of an escape interval of, for example, 10 seconds, starting from the time the patient's last respiratory cycle was sensed by the respiration curve analyzer 78 of the device. Such a rule is illustrated in the respiratory cycle timing graph of FIG. 12.

Referring to that Figure, a 10-second escape interval is selected because it corresponds to the interval between successive ones of a typical 6 respiratory cycles per minute during the sleep state of an individual. When the peak of a respiratory cycle 90 in the sequence of such cycles is sensed, a timed escape interval of 10 seconds is commenced. Immediately prior to the expiration of that interval, at say, 9.5 seconds, the escape interval is reset for another 10 seconds, provided that the next successive respiratory cycle 91 is in process of being sensed. This assures that a burst of electrical stimulation will not be applied prematurely to the phrenic nerves. If, however, no respiratory cycle is sensed following cycle 91 before the expiration of the current 10-second escape interval, it is indicative of a lack of intrinsic ventilation of the patient for that designated sustained period. In that event, the pulse generator 86 is activated by microcontroller 82 to produce a burst of pulses for PNS. In turn, this stimulation of the phrenic nerves produces pacing of the patient's diaphragm 95 (contraction, and attendant expansion of the lungs 96, 97), FIG. 10, to restore breathing by the patient.

Communication between the implanted stimulus generator 65 and external station 84 may be implemented by conventional techniques of telemetry or other wireless communication to accommodate external programming and monitoring. This may include the aforementioned retrieval of data stored in internal memory of the device microcontroller 82 and reprogramming by an attending physician following the initial implantation, and thereafter during office visits by the patient. The arrangement would also accommodate signal transmission to a bedside monitor (not shown) to sound an alarm to awaken the patient for resumption of breathing if the PNS failed to achieve that result through diaphragmatic pacing.

In a preferred method of the present invention, isolation between sensing and stimulation along the phrenic nerve, as well as assurance that the sensed EKG signal is acquired purely from the electrical energy generated by the heart itself, unadulterated by other sources such as the phrenic nerve stimulation (PNS) and its effect on the heart, is achieved by blanking the sense (input) amplifier of the generator 65 during and for the duration of each interval of stimulation. Noise and other artifact detection algorithms may also be utilized, along with conventional low pass filtering (e.g., at 1.5 Hz) for passage of the signals representing normal respiration during sleep while eliminating from the determination of thoracic impedance, such extraneous matter as noise, the bulk of signals from other sources, and other artifacts.

Phrenic nerve signal detection may be used to confirm the occurrence of OSA and to distinguish it from the other forms of sleep apnea. During the ongoing detection of successive respiratory cycles as described above, if the escape interval set from the last respiratory cycle expires before the next respiratory cycle occurs, a check is made of whether or not excitation signals are being transmitted by the phrenic nerve to the diaphragm. If they are, it is indicative that the apnea is not attributable to a lack of diaphragmatic pacing, but rather, to an actual episode of OSA. In that case, the microcontroller 82 in implanted stimulus generator 65 shifts transmittal of electrical excitation by pulse generator 86 in an appropriate burst pattern to electrodes 71a, 71b whereby to stimulate muscle adjacent the soft palate 70 (FIG. 10) of the patient. Simultaneously therewith, microcontroller 82 blocks excitation of the phrenic nerve from the pulse generator 86 that would otherwise have taken place upon expiration of the escape interval. Stimulation of muscle adjacent either side of the soft palate 70 is programmed to increase the muscle tone sufficiently to move the palate from the respiration airway and/or to expand the airway, thereby unblocking the airway for resumption of breathing. When regular respiration cycles are detected from the thoracic impedance information as having resumed, delivery of the therapy is ceased.

The electrical stimulation therapy for all forms of sleep apnea detected by the method of the present invention is preferably pulse excitation instituted by pulse bursts interrupted periodically, albeit very briefly, to allow thoracic impedance/respiratory cycles/ventilation of the patient to be monitored from the sensed EKG signal between bursts, to determine when the delivery of therapy should be ceased.

Electronic means utilized in the implanted device 60 that implements the method of the invention are state of the art, and may be provided in a single microchip or microchip array configuration to accommodate microminiature assembly, with the size of the device being dictated primarily by the battery power required for reliable operation. In addition to other desirable improvements described herein over the prior art, the present invention enables electrical energy generated by the patient's heart to be a primary source for deriving the thoracic impedance/ventilation parameters from the sensed EKG signal, with the result that battery drain is reduced and device lifetime is extended.

A presently contemplated best mode of practicing the invention has been disclosed, but variations and modifications may become apparent to those skilled in the art without departing from the spirit and scope of the invention.

What is claimed is:

1. A method of detecting sleep apnea in a patient, which comprises the steps of:
sensing an EKG signal generated by the patient's heart, amplifying the sensed EKG signal in separate paths of high input impedance and of considerably lower impedance to produce two different signals, and differentially amplifying said two signals to detect changes in the patient's ventilation, to identify the absence of ventilation as a potential episode of sleep apnea.

2. The method of claim 1, including:
sensing consecutive respiration cycles from said detected changes of patient ventilation; establishing a predetermined escape interval of time between pairs of successive respiration cycles and resetting said escape interval upon sensing each respiration cycle, for detecting a sustained absence of ventilation upon expiration of a said escape interval without having detected a next following respiration cycle, as indicative of an actual episode of sleep apnea; and delivering electrical stimulation therapy to restore patient ventilation in response to said indication of an actual episode of sleep apnea.

3. The method of claim 2, including:
delivering said electrical stimulation therapy to the patient's phrenic nerve in response to said indication of an actual episode of sleep apnea, to initiate diaphragmatic pacing and restoration of patient ventilation.

4. The method of claim 3, including:
sensing said EKG signal in the immediate vicinity of the site at which said electrical stimulation is to be applied to the phrenic nerve.

5. The method of claim 4, including:
using at least one of the same electrode for both said sensing and said stimulation.

6. The method of claim 2, wherein:
said episode of sleep apnea is of a type among central sleep apnea (CSA), Cheyne-Stokes Respiration (CSR)-induced apnea, and obstructive sleep apnea (OSA), and including:
distinguishing between an episode of CSA/CSR as constituting one type for treatment purposes and an episode of OSA as constituting another type for treatment purposes, and delivering said electrical stimulation therapy in a manner according to which of said one type and said another type is present in said episode.

7. The method of claim 6, including:
distinguishing an episode of CSA/CSR type from an episode of OSA type of sleep apnea disorder by sensing whether phrenic nerve signals are absent or present, respectively.

8. The method of claim 7, wherein:
said sleep apnea disorder is of CSA/CSR type, and said therapy comprises stimulating the patient's phrenic nerve with electrical pulses in a pattern to produce diaphragmatic pacing for restoration of proper respiration.

9. The method of claim 8, including:
applying said stimulation pulses to both sides of the phrenic nerve sufficiently removed from the site of the heart to avoid interference with heart function.

10. The method of claim 7, wherein:
said sleep apnea disorder is of OSA type, and said therapy comprises stimulating muscle adjacent a projection of the soft palate from the throat of the patient in a stimulation pattern toward toning of said muscle to at least partially remove obstruction of the respiratory airway by the soft palate, and thereby restore more normal respiration.

11. The method of claim 1, including:
providing said separate paths by alternately shunting said high input impedance path with said considerably lower input impedance path at a relatively high switching rate predetermined to provide sufficient resolution to detect patient ventilation and said changes therein.

12. The method of claim 1, including:
sensing said EKG signal at a site of the patient's body remote from the site of the patient's heart.

13. An implantable device-implemented method of evaluating whether an episode of sleep apnea is occurring in a patient, said method comprising the steps of:
sensing the electrical signal generated by the patient's heart with the implanted device,
processing the sensed electrical signal as the sole input to signal processing circuitry of the implanted device to acquire separate high and low input impedance signals therefrom, and differentially amplifying the high and low input impedance signals to determine ventilation of the patient to assess therefrom whether an episode of sleep apnea is occurring.

14. The device-implemented method of claim 13, including:
stimulating the patient's phrenic nerve from the implanted device when the assessment indicates an episode of sleep apnea has commenced.

15. The device-implemented method of claim 13, wherein:
said processing of the sensed electrical signal includes continuously switching application thereof to a high input impedance path and a low input impedance path of said signal processing circuitry at a rate sufficiently rapid to detect patient ventilation and changes therein.

16. The device-implemented method of claim 13, including:
sensing said heart signals at a site of the body removed from the location of the heart.

17. The device-implemented method of claim 13, including:
detecting changes in the patient's ventilation as determined, and identifying an absence of ventilation as a potential episode of sleep apnea.

18. The device-implemented method of claim 17, including:
sensing consecutive respiration cycles from said detected changes in patient ventilation;
establishing a predetermined escape interval of time between pairs of successive respiration cycles and resetting said escape interval upon sensing each respiration cycle;
detecting a sustained absence of ventilation upon expiration of a said escape interval without having detected a next following respiration cycle, as indicative of an actual episode of sleep apnea; and
delivering electrical stimulation therapy to restore patient ventilation in response to said indication of an actual episode of sleep apnea.

19. The device-implemented method of claim 18, including:
delivering said electrical stimulation therapy to the patient's phrenic nerve in response to said indication of an actual episode of sleep apnea, to initiate diaphragmatic pacing and restoration of patient ventilation.

20. The device-implemented method of claim 19, including:
sensing said heart signals in the immediate vicinity of the site at which said electrical stimulation is to be applied to the phrenic nerve.

21. The device-implemented method of claim 20, including:
using at least one of the same electrode of said device for both said heart signal sensing and said phrenic nerve stimulation.

22. The device-implemented method of claim 18, wherein:
said episode of sleep apnea is of a type among central sleep apnea (CSA), Cheyne-Stokes Respiration (CSR)-induced apnea, and obstructive sleep apnea (OSA), and including:
distinguishing between an episode of CSA/CSR as constituting one type for treatment purposes and an episode of OSA as constituting another type for treatment purposes, and delivering said electrical stimulation therapy in a manner according to which of said one type and said another type is present in said episode.

23. The device-implemented method of claim 22, including:
distinguishing an episode of CSA/CSR type from an episode of OSA type of sleep apnea disorder by sensing whether phrenic nerve signals are absent or present, respectively.

24. The device-implemented method of claim 23, wherein:
said sleep apnea disorder is of CSA/CSR type, and
said therapy comprises stimulating the patient's phrenic nerve with electrical pulses in a pattern to produce diaphragmatic pacing for restoration of normal patient respiration.

25. The device-implemented method of claim 20, including:
applying said stimulation pulses to both sides of the phrenic nerve sufficiently removed from the site of the heart to avoid interference with heart function.

26. The device-implemented method of claim 23, wherein:
said sleep apnea disorder is of OSA type, and
said therapy comprises stimulating muscle adjacent a projection of the soft palate from the throat of the patient in a stimulation pattern toward toning of said muscle to at least partially remove obstruction of the respiratory airway by the soft palate, and thereby restore normal patient respiration.

27. The device-implemented method of claim 17, including:
providing separate paths of high input impedance and of considerably lower impedance of said signal processing circuitry to acquire said separate signals in pairs from the sensed electrical signal generated by the patient's heart; and
alternately shunting said high input impedance path with said considerably lower input impedance path at a relatively high switching rate predetermined to provide sufficient resolution to detect patient ventilation and said changes therein.

28. The device-implemented method of claim 13, including:
detecting changes in the patient's ventilation as determined to confirm onset of an actual episode of sleep apnea, including:
analyzing said ventilation changes to detect successive respiratory cycles therefrom, and establishing an escape interval of time of sufficient sustained length between successive respiratory cycles to determine expiration of an escape interval without having detected the next respiratory cycle as signifying a lack of ventilation indicative of an actual episode of sleep apnea.

29. The device-implemented method of claim 28, including:
delivering electrical stimulation therapy to the patient's phrenic nerve from the device in response to said indicated actual episode of sleep apnea, to induce resumption of normal ventilation by the patient.

30. The device-implemented method of claim 29, including
alternately sensing the patient's heart signal and delivering the stimulation therapy at substantially the same site, remote from the patient's heart, and
ceasing delivery of the stimulation therapy upon resumption of normal ventilation.

31. An implantable device-implemented method of detecting sleep apnea in a patient for delivery of therapy to disrupt the detected sleep apnea, which comprises the steps of:
sensing the patient's EKG signal,
alternately applying the sensed signal to a high input impedance path and a considerably lower input impedance path continuously at a relatively rapid switching rate for sufficient resolution to detect patient ventilation and changes therein, and to produce consecutive pairs of signals of different amplitude, and
determining the difference in amplitude between signals of each of said signal pairs by differential processing thereof to detect patient ventilation and changes therein, including the presence or absence of ventilation, to identify commencement of an episode of sleep apnea.

32. The device-implemented method of claim 31, including:
confirming onset of an actual episode of sleep apnea by analyzing said ventilation changes to detect successive respiratory cycles therefrom, establishing an escape interval of time of sufficient sustained length between successive respiratory cycles to determine expiration of an escape interval without having detected the next respiratory cycle as signifying a lack of ventilation indicative of an actual episode of sleep apnea.

33. The device-implemented method of claim 32, including:
delivering electrical stimulation therapy to the patient's phrenic nerve from the device in response to said detected actual episode of sleep apnea, to induce resumption of patient ventilation.

34. The device-implemented method of claim 33, including
sensing the EKG signal and delivering the stimulation therapy at substantially the same site, remote from the patient's heart.

* * * * *

UNITED STATES PATENT AND TRADEMARK OFFICE
CERTIFICATE OF CORRECTION

PATENT NO. : 8,359,097 B2
APPLICATION NO. : 12/931152
DATED : January 22, 2013
INVENTOR(S) : Eckhard Alt et al.

Page 1 of 1

It is certified that error appears in the above-identified patent and that said Letters Patent is hereby corrected as shown below:

In the Claims:

Column 19, line 42, in claim 25, first line, "claim 20" should read -- claim 24 --.

Signed and Sealed this
Thirtieth Day of April, 2013

Teresa Stanek Rea
*Acting Director of the United States Patent and Trademark Office*